United States Patent
Schmitz et al.

(10) Patent No.: US 9,814,484 B2
(45) Date of Patent: Nov. 14, 2017

(54) MICRO DEBRIDER DEVICES AND METHODS OF TISSUE REMOVAL

(71) Applicant: Microfabrica Inc., Van Nuys, CA (US)

(72) Inventors: Gregory P. Schmitz, Los Gatos, CA (US); Gregory B. Arcenio, Redwood City, CA (US); Ronald Leguidleguid, Union City, CA (US); Juan Diego Perea, Campbell, CA (US)

(73) Assignee: Microfabrica Inc., Van Nuys, CA (US)

( * ) Notice: Subject to any disclaimer, the term of this patent is extended or adjusted under 35 U.S.C. 154(b) by 286 days.

(21) Appl. No.: 13/714,285

(22) Filed: Dec. 13, 2012

(65) Prior Publication Data

US 2014/0148835 A1    May 29, 2014

Related U.S. Application Data

(60) Provisional application No. 61/731,434, filed on Nov. 29, 2012.

(51) Int. Cl.
*A61B 17/3207* (2006.01)
*A61B 17/32* (2006.01)
*A61B 17/00* (2006.01)

(52) U.S. Cl.
CPC ........... *A61B 17/320758* (2013.01); *A61B 17/32002* (2013.01); *A61B 2017/00323* (2013.01); *A61B 2017/00473* (2013.01); *A61B 2017/32006* (2013.01); *A61B 2017/320024* (2013.01); *A61B 2017/320775* (2013.01); *A61B 2217/007* (2013.01)

(58) Field of Classification Search
CPC ...... A61B 17/320758; A61B 17/32002; A61B 2017/320766; A61B 2017/320775; A61B 2017/320024; A61B 2017/320032; A61B 2017/320056
USPC ........................................................ 606/170
See application file for complete search history.

(56) References Cited

U.S. PATENT DOCUMENTS

| 1,179,910 A | 4/1916 | Greenfield |
| 1,817,000 A | 8/1931 | Bernard |
| 2,259,015 A | 10/1941 | Anderson et al. |

(Continued)

FOREIGN PATENT DOCUMENTS

| DE | 202008013915 U | 3/2009 |
| EP | 0572131 A1 | 12/1993 |

(Continued)

OTHER PUBLICATIONS

Schmitz et al.; U.S. Appl. No. 14/033,397 entitled "Micro-Mechanical Devices and Methods for Brain Tumor Removal," filed Sep. 20, 2013.

(Continued)

*Primary Examiner* — Tuan V Nguyen
*Assistant Examiner* — Chima Igboko
(74) *Attorney, Agent, or Firm* — Dennis R. Smalley; Douglas C. Limbach

(57) ABSTRACT

A bendable medical device such as for removing tissue from a subject is provided with a distal housing, an outer support tube, an inner drive tube, a coupler and a commutator portion. The coupler and commutator portion serve to axially constrain a distal end of the inner drive tube during bending, and to supply fluid for lubricating, cooling and irrigating the distal end of the device.

1 Claim, 32 Drawing Sheets

(56) References Cited

U.S. PATENT DOCUMENTS

| | | | |
|---|---|---|---|
| 2,455,655 A | 12/1948 | Carroll | |
| 3,404,677 A | 10/1968 | Springer | |
| 3,882,872 A | 5/1975 | Douvas et al. | |
| 3,937,222 A | 2/1976 | Banko | |
| 4,197,645 A | 4/1980 | Schiecher | |
| 4,334,650 A | 6/1982 | Hardwick et al. | |
| 4,598,710 A | 7/1986 | Kleinberg et al. | |
| 4,621,637 A | 11/1986 | Fishbein | |
| 4,747,821 A | 5/1988 | Kensey et al. | |
| 4,804,364 A * | 2/1989 | Dieras et al. | 604/22 |
| 4,842,578 A | 6/1989 | Johnson et al. | |
| 4,844,363 A | 7/1989 | Garnier et al. | |
| 4,854,808 A | 8/1989 | Bisiach | |
| 4,943,296 A | 7/1990 | Funakubo et al. | |
| 4,983,179 A | 1/1991 | Sjostrom | |
| 4,986,807 A | 1/1991 | Farr | |
| 5,019,088 A | 5/1991 | Farr | |
| 5,084,052 A | 1/1992 | Jacobs | |
| 5,141,168 A | 8/1992 | Pepper | |
| 5,160,095 A | 11/1992 | Pepper | |
| 5,181,433 A | 1/1993 | Ueno et al. | |
| 5,190,637 A | 3/1993 | Guckel | |
| 5,226,909 A | 7/1993 | Evans et al. | |
| 5,284,486 A | 2/1994 | Kotula et al. | |
| 5,378,583 A | 1/1995 | Guckel et al. | |
| 5,411,511 A | 5/1995 | Hall | |
| 5,465,444 A | 11/1995 | Bigler et al. | |
| 5,484,112 A | 1/1996 | Koenig | |
| 5,496,668 A | 3/1996 | Guckel et al. | |
| 5,522,829 A | 6/1996 | Michalos | |
| 5,549,637 A | 8/1996 | Crainich | |
| 5,575,799 A | 11/1996 | Bolanos et al. | |
| 5,576,147 A | 11/1996 | Guckel et al. | |
| 5,591,187 A | 1/1997 | Dekel | |
| 5,601,556 A | 2/1997 | Pisharodi | |
| 5,618,293 A | 4/1997 | Sample et al. | |
| 5,643,304 A | 7/1997 | Schechter et al. | |
| 5,662,284 A | 9/1997 | Koenig | |
| 5,676,321 A | 10/1997 | Kroger | |
| 5,685,838 A | 11/1997 | Peters et al. | |
| 5,693,063 A | 12/1997 | Van Wyk et al. | |
| 5,695,510 A | 12/1997 | Hood | |
| 5,718,618 A | 2/1998 | Guckel et al. | |
| 5,725,530 A | 3/1998 | Popken | |
| 5,779,713 A | 7/1998 | Turjanski et al. | |
| 5,782,848 A | 7/1998 | Lennox | |
| 5,788,169 A | 8/1998 | Koenig | |
| 5,810,809 A | 9/1998 | Rydell | |
| 5,823,990 A | 10/1998 | Henley | |
| 5,846,244 A | 12/1998 | Cripe | |
| 5,863,294 A | 1/1999 | Alden | |
| 5,866,281 A | 2/1999 | Guckel et al. | |
| 5,908,719 A | 6/1999 | Guckel et al. | |
| 5,910,150 A | 6/1999 | Saadat | |
| 5,916,231 A | 6/1999 | Bays | |
| 5,928,158 A | 7/1999 | Aristides | |
| 5,928,161 A | 7/1999 | Krulevitch et al. | |
| 5,957,881 A | 9/1999 | Peters et al. | |
| 6,001,112 A * | 12/1999 | Taylor | 606/159 |
| 6,010,477 A | 1/2000 | Bays | |
| 6,013,991 A | 1/2000 | Philipp | |
| 6,027,630 A | 2/2000 | Cohen | |
| 6,063,088 A | 5/2000 | Winslow | |
| 6,129,698 A | 10/2000 | Beck | |
| 6,190,385 B1 | 2/2001 | Tom et al. | |
| 6,217,598 B1 | 4/2001 | Berman | |
| 6,221,088 B1 | 4/2001 | Bays | |
| 6,238,405 B1 * | 5/2001 | Findlay et al. | 606/159 |
| 6,293,957 B1 | 9/2001 | Peters et al. | |
| 6,402,070 B1 | 6/2002 | Ishida et al. | |
| 6,447,525 B2 | 9/2002 | Follmer et al. | |
| 6,454,717 B1 * | 9/2002 | Pantages et al. | 600/466 |
| 6,475,369 B1 | 11/2002 | Cohen | |
| 6,503,263 B2 | 1/2003 | Adams | |
| 6,517,544 B1 | 2/2003 | Michelson | |
| 6,565,588 B1 | 5/2003 | Clement et al. | |
| 6,572,613 B1 | 6/2003 | Ellman et al. | |
| 6,572,742 B1 | 6/2003 | Cohen | |
| 6,613,972 B2 | 9/2003 | Cohen et al. | |
| 6,663,031 B2 | 12/2003 | Henderson et al. | |
| 6,666,874 B2 | 12/2003 | Heitzmann et al. | |
| 6,753,952 B1 | 6/2004 | Lawrence et al. | |
| 6,761,723 B2 | 7/2004 | Buttermann et al. | |
| 6,790,377 B1 | 9/2004 | Cohen | |
| 6,951,456 B2 | 10/2005 | Cohen et al. | |
| 6,966,912 B2 | 11/2005 | Michelson | |
| 6,994,708 B2 | 2/2006 | Manzo | |
| 7,052,494 B2 | 5/2006 | Goble et al. | |
| 7,160,304 B2 | 1/2007 | Michelson | |
| 7,163,614 B2 | 1/2007 | Cohen | |
| 7,195,989 B2 | 3/2007 | Lockard et al. | |
| 7,229,544 B2 | 6/2007 | Cohen | |
| 7,235,088 B2 | 6/2007 | Pinto et al. | |
| 7,239,219 B2 | 7/2007 | Brown et al. | |
| 7,252,861 B2 | 8/2007 | Smalley | |
| 7,479,147 B2 | 1/2009 | Honeycutt et al. | |
| 7,540,867 B2 | 6/2009 | Jinno et al. | |
| 7,553,307 B2 | 6/2009 | Bleich et al. | |
| 7,699,790 B2 | 4/2010 | Simpson | |
| 7,918,849 B2 | 4/2011 | Bleich et al. | |
| 8,002,776 B2 | 8/2011 | Liu et al. | |
| 8,034,003 B2 | 10/2011 | Pesce et al. | |
| 8,114,074 B1 | 2/2012 | Slater | |
| 8,146,400 B2 | 4/2012 | Goldfarb et al. | |
| 8,292,889 B2 | 10/2012 | Cunningham et al. | |
| 8,326,414 B2 | 12/2012 | Neubardt et al. | |
| 8,361,094 B2 * | 1/2013 | To et al. | 606/159 |
| 8,409,235 B2 | 4/2013 | Rubin | |
| 8,414,606 B2 | 4/2013 | Shadeck et al. | |
| 8,414,607 B1 | 4/2013 | Lockard et al. | |
| 8,486,096 B2 | 7/2013 | Robertson et al. | |
| 8,512,342 B2 | 8/2013 | Meredith | |
| 8,702,702 B1 | 4/2014 | Edwards et al. | |
| 8,715,281 B2 | 5/2014 | Barlow et al. | |
| 2001/0000531 A1 | 4/2001 | Casscells et al. | |
| 2001/0041307 A1 | 11/2001 | Lee et al. | |
| 2002/0058944 A1 | 5/2002 | Michelson | |
| 2002/0099367 A1 | 7/2002 | Guo et al. | |
| 2002/0123763 A1 | 9/2002 | Blake | |
| 2002/0138088 A1 * | 9/2002 | Nash et al. | 606/159 |
| 2003/0144681 A1 | 7/2003 | Sample | |
| 2003/0163126 A1 | 8/2003 | West | |
| 2003/0179364 A1 | 9/2003 | Steenblik et al. | |
| 2004/0138672 A1 | 7/2004 | Michelson | |
| 2005/0021065 A1 | 1/2005 | Yamada et al. | |
| 2005/0029109 A1 | 2/2005 | Zhang et al. | |
| 2005/0054972 A1 | 3/2005 | Adams et al. | |
| 2005/0059905 A1 | 3/2005 | Boock et al. | |
| 2005/0090848 A1 | 4/2005 | Adams | |
| 2005/0222598 A1 | 10/2005 | Ho et al. | |
| 2006/0089662 A1 | 4/2006 | Davison et al. | |
| 2006/0161185 A1 | 7/2006 | Saadat et al. | |
| 2006/0184175 A1 | 8/2006 | Schomer et al. | |
| 2006/0200152 A1 | 9/2006 | Karubian et al. | |
| 2006/0212060 A1 | 9/2006 | Hacker et al. | |
| 2006/0217730 A1 | 9/2006 | Termanini | |
| 2006/0224160 A1 | 10/2006 | Trieu et al. | |
| 2006/0229624 A1 | 10/2006 | May et al. | |
| 2006/0229646 A1 | 10/2006 | Sparks | |
| 2006/0241566 A1 | 10/2006 | Moon et al. | |
| 2006/0276782 A1 | 12/2006 | Gedebou | |
| 2006/0282065 A1 | 12/2006 | Cohen | |
| 2007/0016225 A1 | 1/2007 | Nakao | |
| 2007/0073303 A1 | 3/2007 | Namba | |
| 2007/0100361 A1 | 5/2007 | Cohen | |
| 2007/0162062 A1 | 7/2007 | Norton et al. | |
| 2007/0173872 A1 | 7/2007 | Neuenfeldt | |
| 2007/0197895 A1 | 8/2007 | Nycz et al. | |
| 2007/0198038 A1 | 8/2007 | Cohen et al. | |
| 2007/0219459 A1 | 9/2007 | Cohen | |
| 2007/0260253 A1 | 11/2007 | Johnson et al. | |
| 2007/0265648 A1 | 11/2007 | Cohen | |
| 2008/0004643 A1 * | 1/2008 | To et al. | 606/159 |
| 2008/0009697 A1 | 1/2008 | Haider et al. | |

(56) References Cited

U.S. PATENT DOCUMENTS

| | | | |
|---|---|---|---|
| 2008/0027427 A1 | 1/2008 | Falkenstein et al. | |
| 2008/0065125 A1* | 3/2008 | Olson | 606/159 |
| 2008/0091074 A1 | 4/2008 | Kumar et al. | |
| 2008/0091224 A1 | 4/2008 | Griffis et al. | |
| 2008/0103504 A1 | 5/2008 | Schmitz et al. | |
| 2008/0161809 A1 | 7/2008 | Schmitz et al. | |
| 2008/0249553 A1 | 10/2008 | Gruber et al. | |
| 2009/0012524 A1 | 1/2009 | Dower | |
| 2009/0018565 A1* | 1/2009 | To et al. | 606/159 |
| 2009/0018566 A1* | 1/2009 | Escudero et al. | 606/159 |
| 2009/0124975 A1 | 5/2009 | Oliver et al. | |
| 2009/0228030 A1 | 9/2009 | Shadeck | |
| 2009/0234378 A1* | 9/2009 | Escudero et al. | 606/180 |
| 2009/0270812 A1* | 10/2009 | Litscher et al. | 604/164.01 |
| 2009/0306773 A1 | 12/2009 | Silvestrini et al. | |
| 2010/0010492 A1 | 1/2010 | Lockard et al. | |
| 2010/0010525 A1 | 1/2010 | Lockard et al. | |
| 2010/0030216 A1 | 2/2010 | Arcenio | |
| 2010/0094320 A1 | 4/2010 | Arat et al. | |
| 2010/0152758 A1 | 6/2010 | Mark et al. | |
| 2010/0160916 A1 | 6/2010 | Chana et al. | |
| 2010/0191266 A1 | 7/2010 | Oliver et al. | |
| 2010/0204560 A1 | 8/2010 | Salahieh et al. | |
| 2010/0217268 A1 | 8/2010 | Bloebaum et al. | |
| 2010/0305595 A1 | 12/2010 | Hermann | |
| 2011/0112563 A1* | 5/2011 | To et al. | 606/159 |
| 2011/0190738 A1 | 8/2011 | Zemlok et al. | |
| 2011/0230727 A1 | 9/2011 | Sanders et al. | |
| 2011/0288573 A1 | 11/2011 | Yates et al. | |
| 2012/0041263 A1 | 2/2012 | Sholev | |
| 2012/0053606 A1 | 3/2012 | Schmitz et al. | |
| 2012/0071752 A1 | 3/2012 | Sewell et al. | |
| 2012/0109024 A1 | 5/2012 | Theuer | |
| 2012/0109172 A1* | 5/2012 | Schmitz et al. | 606/170 |
| 2012/0178985 A1 | 7/2012 | Walters et al. | |
| 2012/0191116 A1 | 7/2012 | Flynn et al. | |
| 2012/0191121 A1 | 7/2012 | Chen et al. | |
| 2012/0221035 A1 | 8/2012 | Harvey | |
| 2013/0012975 A1 | 1/2013 | Schmitz et al. | |
| 2013/0226209 A1 | 8/2013 | Lockard et al. | |
| 2014/0350567 A1 | 11/2014 | Schmitz et al. | |
| 2015/0173788 A1 | 6/2015 | Lockard et al. | |
| 2016/0135831 A1 | 5/2016 | Schmitz et al. | |
| 2017/0014148 A1 | 1/2017 | Schmitz et al. | |

FOREIGN PATENT DOCUMENTS

| | | |
|---|---|---|
| EP | 0925857 A2 | 6/1999 |
| EP | 1256319 A2 | 11/2002 |
| EP | 1026996 B1 | 10/2007 |
| WO | WO93/05719 A1 | 4/1993 |
| WO | WO99/63891 A1 | 12/1999 |
| WO | WO02/49518 A2 | 6/2002 |
| WO | WO02/062226 A1 | 8/2002 |
| WO | WO2004/069498 A2 | 8/2004 |
| WO | WO 2008/037984 A2 | 4/2008 |
| WO | WO 2012/040432 A1 | 3/2012 |

OTHER PUBLICATIONS

Chen et al.; U.S. Appl. No. 14/181,247 entitled "Concentric Cutting Devices for Use in Minimally Invasive Medical Procedures," filed Feb. 14, 2014.

Cohen et al.; EFAB: Batch production of functional, fully-dense metal parts with micron-scale features; Proc 9th, Solid Freeform Fabrication; Univ. of Texas at Austin; pp. 161-168; Aug. 1998.

Cohen et al.; EFAB: low-cost automated electrochemical batch fabrication of abritrary 3-D microstructures; Micromachining and Microfabrication Process Technology, SPIE 1999 Symposium on Micromachining and Microfabrication; 11 pgs.; Sep. 1999.

Cohen et al.; EFAB: Rapid, low-cost desktop micromachining of high aspect ratio true 3-D MEMS; Proc. 12th, IEEE Micro Electro Mechanical Systems Workshop; IEEE; pp. 244-251; Jan. 1999.

Cohen, Adam L.; 3-D micromachining by electrochemical fabrication; Micromachine Devices; pp. 6-7; Mar. 1999.

Cohen, Adam L.; Electrochemical Fabrication (EFAB}); MEMS Handbook; Chapter 19; CRC Press LLC; pp. 19-1-19-23; Jan. 7, 2002.

Microfabrication—rapid prototyping's killer application; Rapid Prototyping Report; vol. 9; No. 6; pp. 1-5; Jun. 1999.

SSI Shredding Systems; www.ssiworld.com; 16 pgs.; Sep. 24, 2009 (downloaded).

Tseng et al.; EFAB: high aspect ratio, arbitrary 3-D metal microstructures using a low-cost automated batch process; 3rd Int'l. Workshop on High Aspect Ratio Microstructure Technology (HARMST99); Kazusa, Japan; 4 pgs.; Jun. 1999.

Tseng et al.; EFAB: high aspect ratio, arbitrary 3-D metal microstructures using a low-cost automated batch process; Microelectromechanical Systems (MEMS); vol. 1; ASME 1999 (Int'l. Mechanical Engineering Congress and Exposition; 6 pgs.; Nov. 1999.

Zhang et al.; EFAB: rapid desktop manufacturing of true 3-D microstructures; Proc. 2nd Int'l. Conf. on Integrated MicroNanotechnology for Space Applications; The Aerospace Co.; 11 pgs.; Apr. 1999.

Schmitz et al.; U.S. Appl. No. 14/333,458 entitled "Counterfeiting deterent and security devices, systems, and methods," filed Jul. 16, 2014.

Schmitz et al.; U.S. Appl. No. 14/440,088 entitled "Micro-mechanical device and method for obstructive sleep apnea treatment," filed May 1, 2015.

Jho et al.; Endoscopy assisted transsphenoidal surgery for pituitary adenoma; Acta Neurochirurgica; 138(12); pp. 1416-1425; 1996 (year of pub. sufficiently earlier than effective US filing date and any foreign priority date).

Bovie Medical Corporation; Resistick II(TM) Coated Electrodes (product information); 2 pgs.; retrieved from the internet (http://www.boviemedical.com/products_aaronresistickelect.asp); print/retrieval date: Apr. 6, 2016.

Schmitz et al.; U.S. Appl. No. 15/292,029 entitled "Surgical micro-shears and methods of fabrication and use," filed Oct. 12, 2016.

* cited by examiner

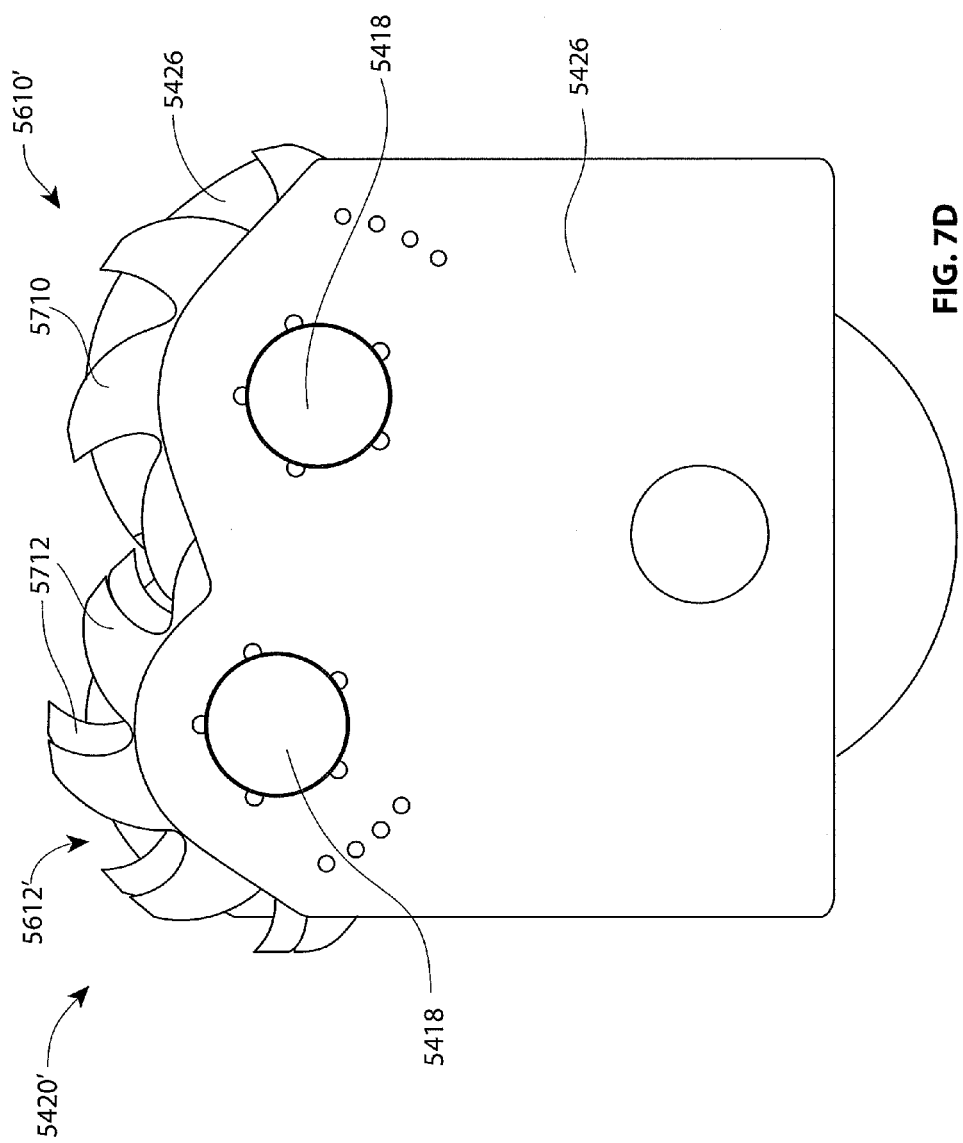

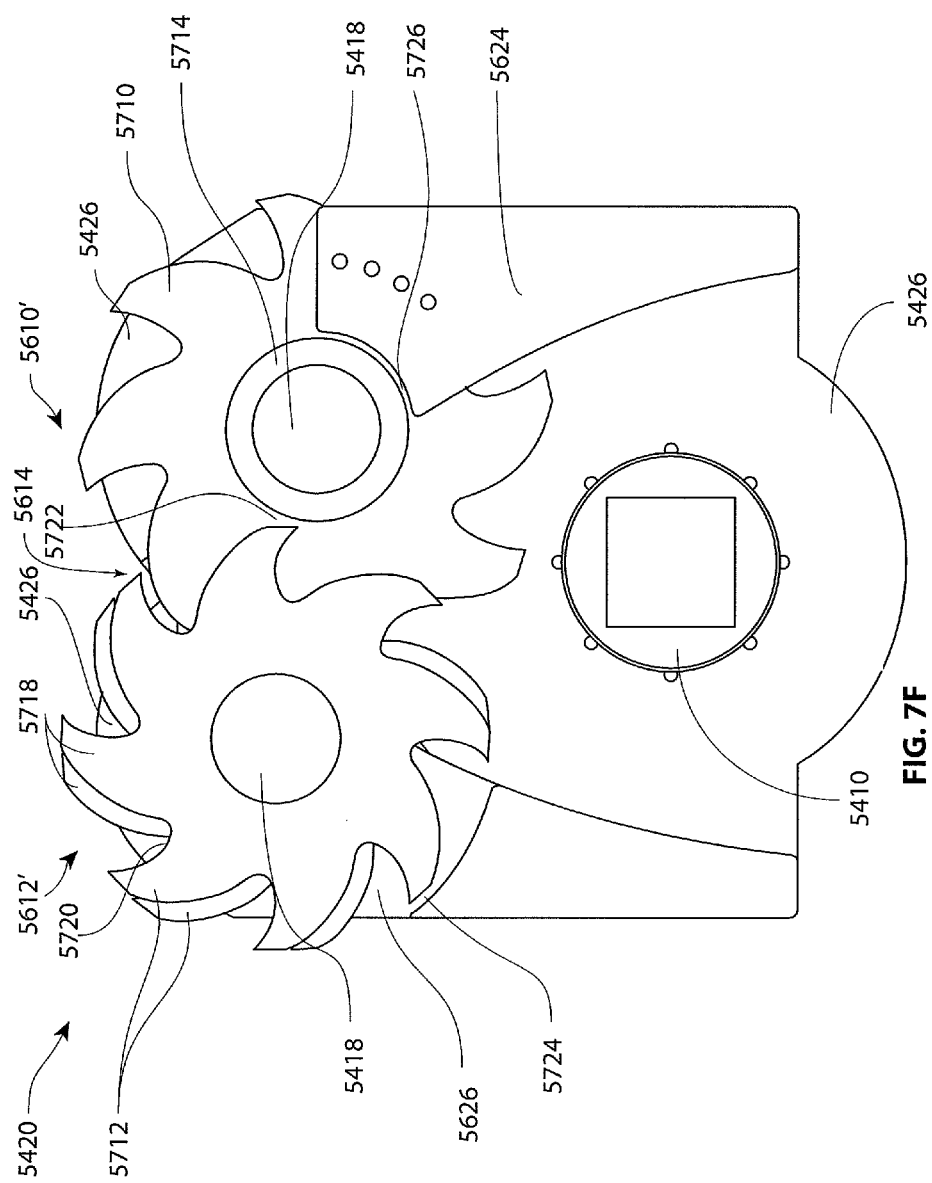

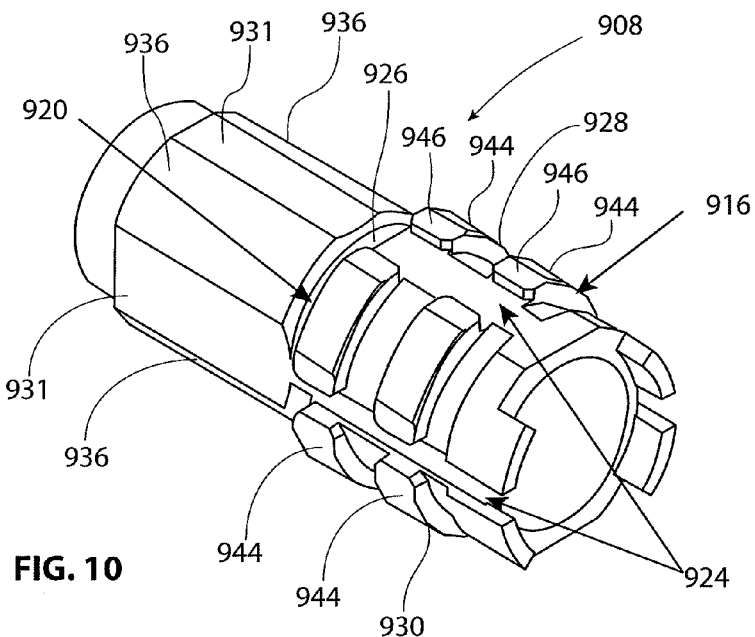
FIG. 10
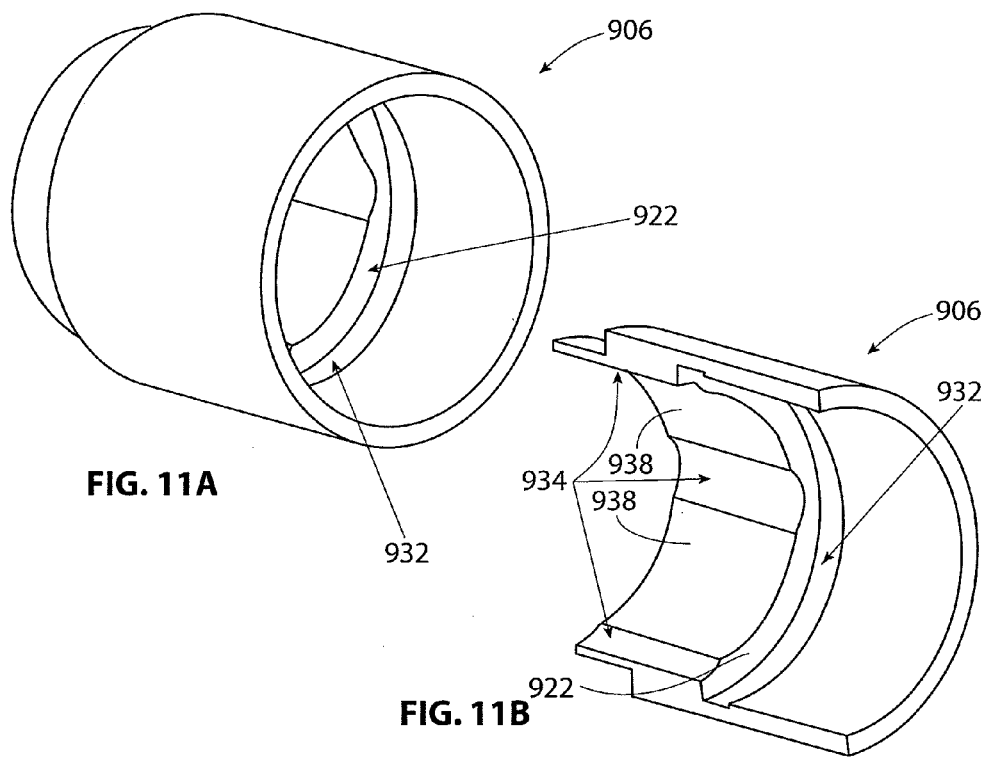
FIG. 11A
FIG. 11B

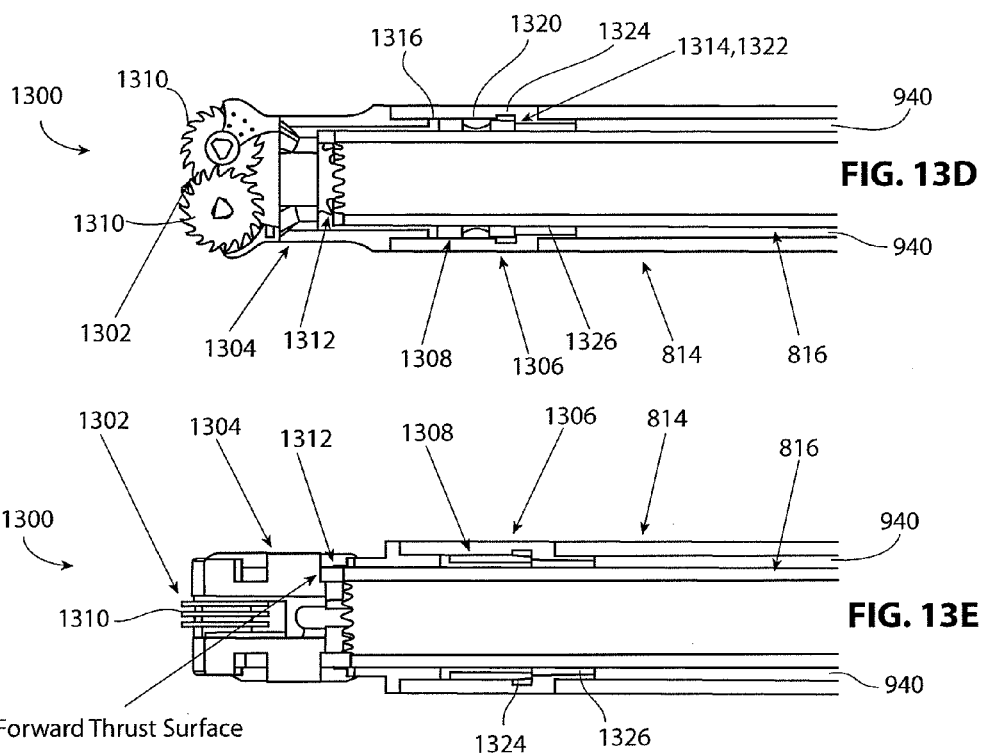
FIG. 13D
FIG. 13E
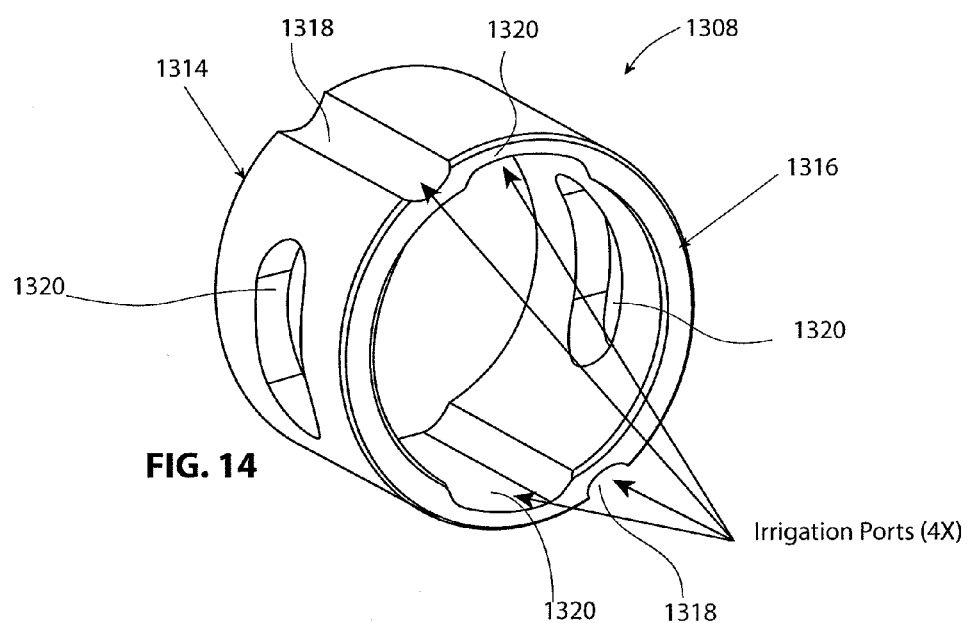
FIG. 14

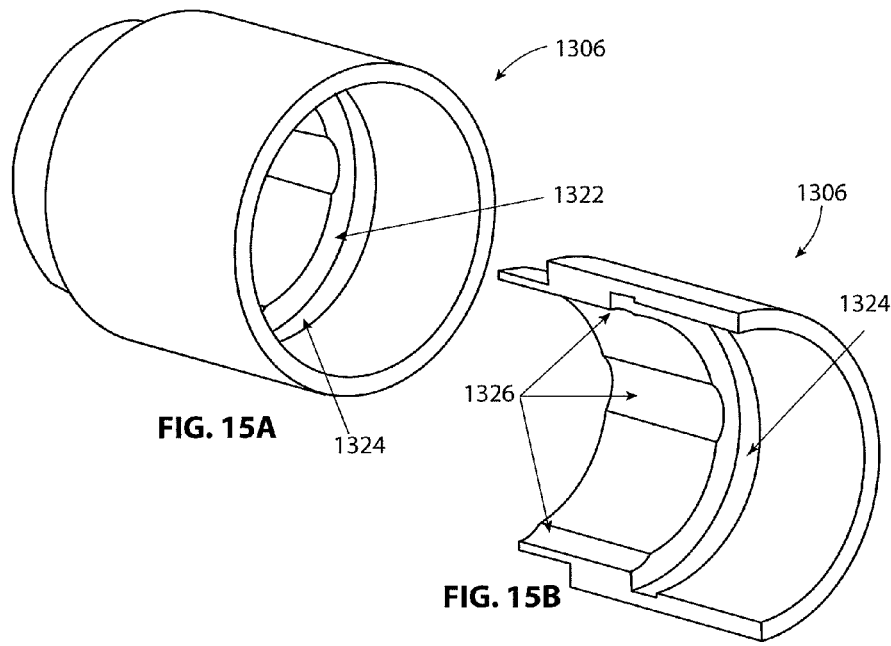
FIG. 15A
FIG. 15B
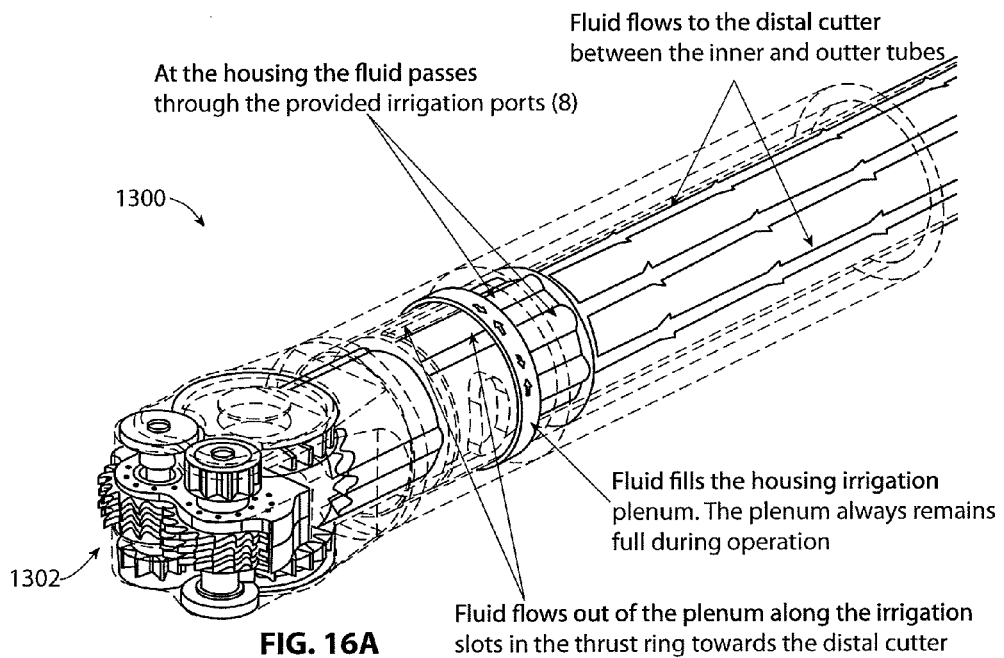
FIG. 16A

Irrigation flow over journal bearing surfaces

MICRO DEBRIDER DEVICES AND METHODS OF TISSUE REMOVAL

CROSS REFERENCE TO RELATED APPLICATIONS

This applications claims priority to U.S. Provisional Application No. 61/731,434 filed on Nov. 29, 2012.

This application is related to the following U.S. applications: application Ser. No. 13/007,578 filed Jan. 14, 2011, now U.S. Pat. No. 8,795,278; application Ser. No. 12/490,295 filed Jun. 23, 2009, now U.S. Pat. No. 8,968,346; Provisional Application No. 61/075,006 filed Jun. 23, 2008; Provisional Application No. 61/164,864 filed Mar. 30, 2009; Provisional Application No. 61/164,883 filed Mar. 30, 2009; application Ser. No. 12/490,301 filed Jun. 23, 2009, now U.S. Pat. No. 8,475,458; Provisional Application No. 61/075,006 filed Jun. 23, 2008; Provisional Application No. 61/164,883 filed Mar. 30, 2009; Provisional Application No. 61/408,558 filed Oct. 29, 2010; Provisional Application No. 61/710,608 filed Oct. 5, 2012; application Ser. No. 13/289,994 filed Nov. 11, 2011, now U.S. Pat. No. 8,475,483; application Ser. No. 13/659,734 filed Oct. 24, 2012; application Ser. No. 13/388,653 filed Apr. 16, 2012; application Ser. No. 12/491,220 filed on Jun. 24, 2009, now U.S. Pat. No. 8,414,607, and application Ser. No. 13/535,197 filed Jun. 27, 2012, now U.S. Pat. No. 9,451,977.

INCORPORATION BY REFERENCE

All publications and patent applications mentioned in this specification are herein incorporated by reference to the same extent as if each individual publication or patent application was specifically and individually indicated to be incorporated by reference.

FIELD

Embodiments of the present disclosure relate to micro-scale and millimeter-scale tissue debridement devices that may, for example, be used to remove unwanted tissue or other material from selected locations within a body of a patient during a minimally invasive or other medical procedure, and in particular embodiments, multi-layer, multi-material electrochemical fabrication methods that are used to, in whole or in part, form such devices.

BACKGROUND

Debridement is the medical removal of necrotic, cancerous, damaged, infected or otherwise unwanted tissue. Some medical procedures include, or consist primarily of, the mechanical debridement of tissue from a subject. Rotary debrider devices have been used in such procedures for many years.

Some debrider devices with relatively large dimensions risk removing unintended tissue from the subject, or damaging the unintended tissue. There is a need for tissue removal devices which have small dimensions and improved functionality which allow them to more safely remove only the desired tissue from the patient. There is also a need for tissue removal devices which have small dimensions and improved functionality over existing products and procedures which allow them to more efficiently remove tissue from the patient.

Prior art tissue removal devices often remove tissue in large pieces, having dimensions well over 2 mm. The tissue pieces are removed through an aspiration lumen typically 3.5 to 5 mm in diameter. Since the tissue pieces being removed commonly have dimensions that are 1 to 2 lumen diameters in length, the tissue pieces can often clog the tissue removal lumen.

One portion of the body in which tissue can be removed to treat a variety of conditions is the spine area. Tissue removal devices for the spine are needed that can be produced with sufficiently small dimensions and/or that have increased performance over existing techniques. For example, a herniated disc or bulging disc can be treated by performing a discectomy, e.g. by removing all or part of the nucleus pulposus of the damaged disc. Such procedures may also involve a laminotomy or laminectomy wherein a portion or all of a lamina may be removed to allow access to the herniated disc. Artificial disc replacement (total or partial) is another example of a procedure which requires the removal of all or a portion of the disc, which is replaced with an artificial device or material.

Tissue removal devices are needed which can be produced with sufficient mechanical complexity and a small size so that they can both safely and more efficiently remove tissue from a subject at a high removal rate, and/or remove tissue in a less invasive procedure and/or with less damage to adjacent tissue such that risks are lowered and recovery time is improved.

SUMMARY OF THE DISCLOSURE

According to some aspects of the disclosure, a medical device for removing tissue from a subject is provided. One exemplary device includes a distal housing, an elongate member, a coupler and a commutator portion. The distal housing is configured with a tissue cutter assembly. The elongate member is coupled to the distal housing and configured to introduce the distal housing to a target tissue site of the subject. The elongate member has an outer tube, an inner drive tube rotatably mounted within the outer tube, and an annular void formed between the inner drive tube and the outer tube. The outer tube and the distal housing form a stator assembly. The coupler is located at a distal end of the inner drive tube and is rotationally coupled therewith to form a rotor assembly. The coupler is configured to engage with the tissue cutter assembly to rotatably drive the tissue cutter assembly. The coupler has a rear thrust surface configured to cooperate with a first surface on the stator assembly to prevent the inner drive tube from moving proximally beyond a predetermined rear location. The coupler also has a forward thrust surface configured to cooperate with a second surface on the stator assembly to prevent the inner drive tube from moving distally beyond a predetermined forward location. The commutator portion is located between the rotor assembly and the stator assembly, and has at least one solid region configured to rotatably support the rotor assembly relative to the stator assembly. The commutator portion has at least one fluid channel configured to allow passage of a fluid from the annular void, distally across the commutator portion, and into a first fluid plenum adjacent to the rear thrust surface and the first surface of the stator assembly. The coupler and the distal housing form at least one passage therebetween that fluidically connects the first fluid plenum with a second fluid plenum adjacent to the forward thrust surface and the second surface of the stator assembly. The device is configured to allow a fluid to flow distally through the annular void, through the at least one fluid channel in the commutator portion, through the first fluid plenum, through the at least one passage between the coupler and the distal housing, through the second fluid plenum, into at least a portion of the tissue cutter assembly, and proximally through the inner drive tube. The device is configured to allow the fluid to lubricate and cool the forward and rear thrust surfaces and the tissue cutter assembly, and to transport tissue pieces cut by the tissue cutter assembly proximally through the inner drive tube.

In some embodiments of the above exemplary device, the commutator portion is located on the coupler. In some embodiments, the commutator portion is located on the distal housing. The commutator portion may be located on both the coupler and the distal housing. In some embodiments, the commutator portion includes a radially outwardly protruding bearing surface configured to rotate relative to and bear against a portion of the stator assembly, and a radially inwardly protruding surface at least partially defining the at least one fluid channel across the commutator portion.

In some embodiments, the coupler is integrally formed on the distal end of the inner drive tube. In other embodiments, the coupler is a separate piece attached to the distal end of the inner drive tube.

In some embodiments, the rotor assembly includes a third plenum axially located between the first plenum and the second plenum. The third plenum may be formed in the coupler and encircle the coupler, and/or be formed in the distal housing and encircle the distal housing.

In some embodiments, the inner drive tube has a proximal end that is axially unconstrained so that it may move axially relative to a proximal end of the outer tube. At least a portion of both the inner drive tube and outer tube may be bendable. In some embodiments, at least a portion of at least one of the inner drive tube and outer tube is malleable. In some embodiments, a first portion of the elongate member telescopes within a second portion of the elongate member. In some embodiments, a first portion of the elongate member articulates around at least one transverse pivot axis relative to a second portion of the elongate member.

Another exemplary device includes a distal housing, an elongate member, a crown gear, a thrust ring and a commutator portion. In this embodiment, the distal housing is configured with a tissue cutter assembly. The elongate member is coupled to the distal housing and is configured to introduce the distal housing to a target tissue site of the subject. The elongate member has an outer tube, an inner drive tube rotatably mounted within the outer tube, and an annular void formed between the inner drive tube and the outer tube. The outer tube and the distal housing form a stator assembly. The crown gear is located on a distal end of the inner drive tube. The coupler is configured to engage a right angle gear of the tissue cutter assembly to rotatably drive the tissue cutter assembly. The thrust ring is rigidly affixed around the inner drive tube near the distal end of the drive tube. The thrust ring has a rear thrust surface configured to cooperate with a first surface on the stator assembly to prevent the inner drive tube from moving proximally beyond a predetermined rear location. The commutator portion is located between the inner drive tube and the stator assembly, and has at least one solid region configured to rotatably support the inner drive tube relative to the stator assembly. The commutator portion has at least one fluid channel configured to allow passage of a fluid from the annular void, distally across the commutator portion, and into a first fluid plenum adjacent to the rear thrust surface and the first surface of the stator assembly. The thrust ring and the distal housing form at least one passage therebetween that is in fluid communication with the first fluid plenum. The device is configured to allow a fluid to flow distally through the annular void, through the at least one fluid channel in the commutator portion, through the first fluid plenum, through the at least one passage between the thrust ring and the distal housing, into at least a portion of the tissue cutter assembly, and proximally through the inner drive tube. The device is configured to allow the fluid to lubricate and cool the rear thrust surface and the tissue cutter assembly, and to transport tissue pieces cut by the tissue cutter assembly proximally through the inner drive tube.

In some embodiments of the exemplary device immediately above, the commutator portion is located on the distal housing. The commutator portion may include a radially inwardly protruding bearing surface configured to bear against a portion of the inner drive tube, thereby radially constraining the inner drive tube while permitting it to freely rotate. The commutator portion may also include a radially outwardly protruding surface at least partially defining the at least one fluid channel across the commutator portion.

In some embodiments, the thrust ring is rigidly affixed to the inner drive tube with at least one weldment inside a preformed hole through a wall of the thrust ring. In some embodiments, the first fluid plenum is formed in the distal housing and encircles the distal housing. The crown gear and the right angle gear may be configured to cooperate to prevent the inner drive tube from moving distally beyond a predetermined forward location.

In some embodiments, the tissue cutter assembly comprises a first rotor and a second, oppositely rotating rotor. Each of the first and second rotors may be configured to rotate about an axis that is perpendicular to a central longitudinal axis of the elongate member. Each of the first and second rotors may have a plurality of blades, wherein the blades of the first rotor are configured to interdigitate with the blades of second rotor.

In some embodiments, the inner drive tube has a proximal end that is axially unconstrained so that it may move axially relative to a proximal end of the outer tube. At least a portion of both the inner drive tube and outer tube may be bendable. In some embodiments, at least a portion of at least one of the inner drive tube and outer tube is malleable. In some embodiments, a first portion of the elongate member telescopes within a second portion of the elongate member. In some embodiments, a first portion of the elongate member articulates around at least one transverse pivot axis relative to a second portion of the elongate member.

Other aspects of the disclosure will be understood by those of skill in the art upon review of the teachings herein. Other aspects of the disclosure may involve combinations of the above noted aspects of the disclosure. These other aspects of the disclosure may provide various combinations of the aspects presented above as well as provide other configurations, structures, functional relationships, and processes that have not been specifically set forth above.

BRIEF DESCRIPTION OF THE DRAWINGS

FIGS. 7A-7F show details of an exemplary rotor housing assembly 5420'.

FIG. 10 is an enlarged perspective view of coupler 908 of device 900.

FIG. 11A is an enlarged perspective view of housing 906 of device 900.

FIG. 11B is an enlarged perspective cross-sectional view of housing 906 of device 900.

FIGS. 13A-13E are various views showing the distal end of a dual, right angle shredder device 1300.

FIG. 14 is an enlarged perspective view of thrust ring 1308 of the device 1300.

FIG. 15A is an enlarged perspective view of housing 1306 of device 1300.

FIG. 15B is an enlarged perspective cross-sectional view of housing 1306 of device 1300.

FIGS. 16A-16E are various views showing the flow of fluid through device 1300.

DETAILED DESCRIPTION

Figure 1:
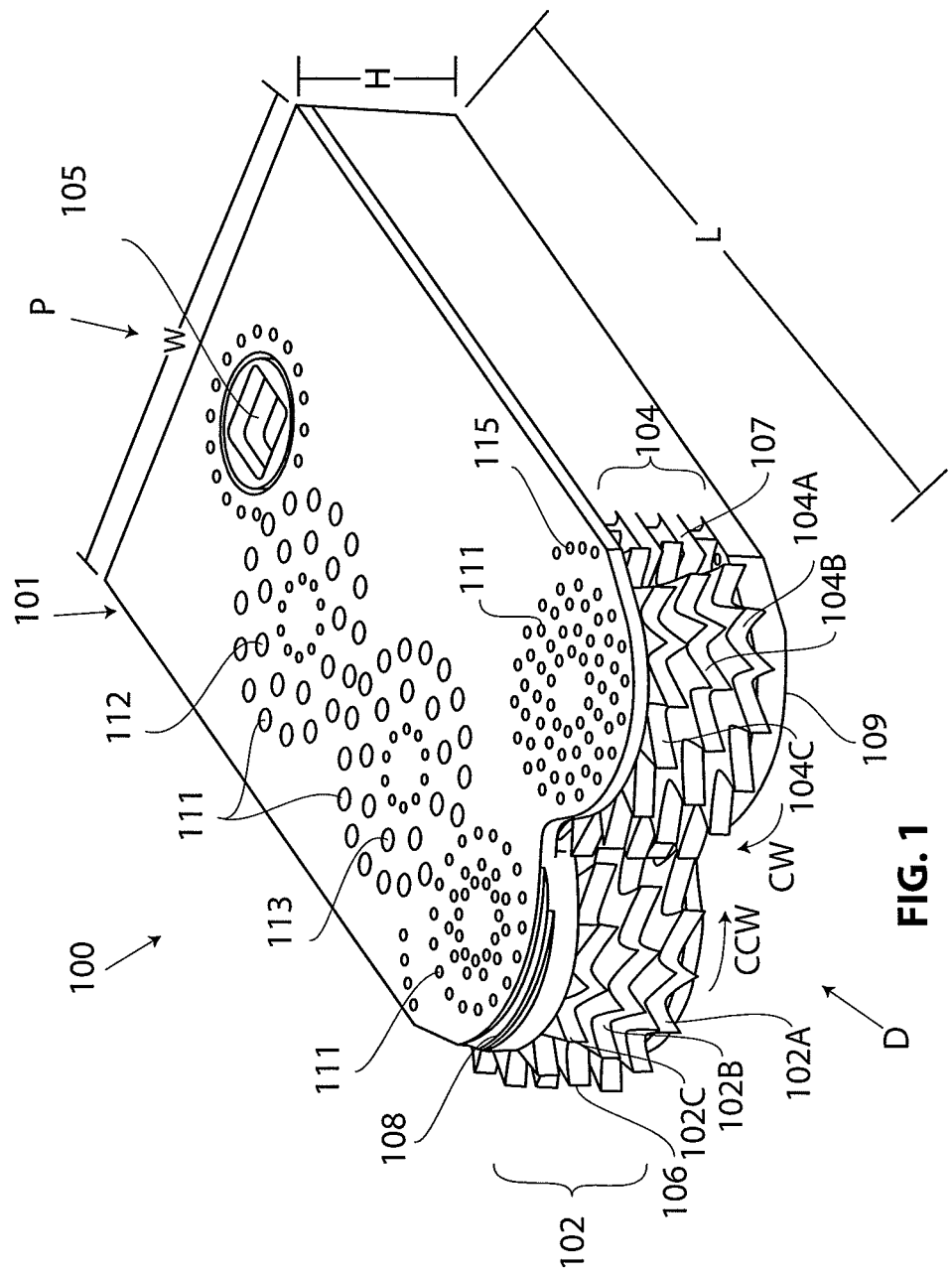
FIGS. 1-3 illustrate an exemplary embodiment of a working end of a tissue removal device.
Figure 2:
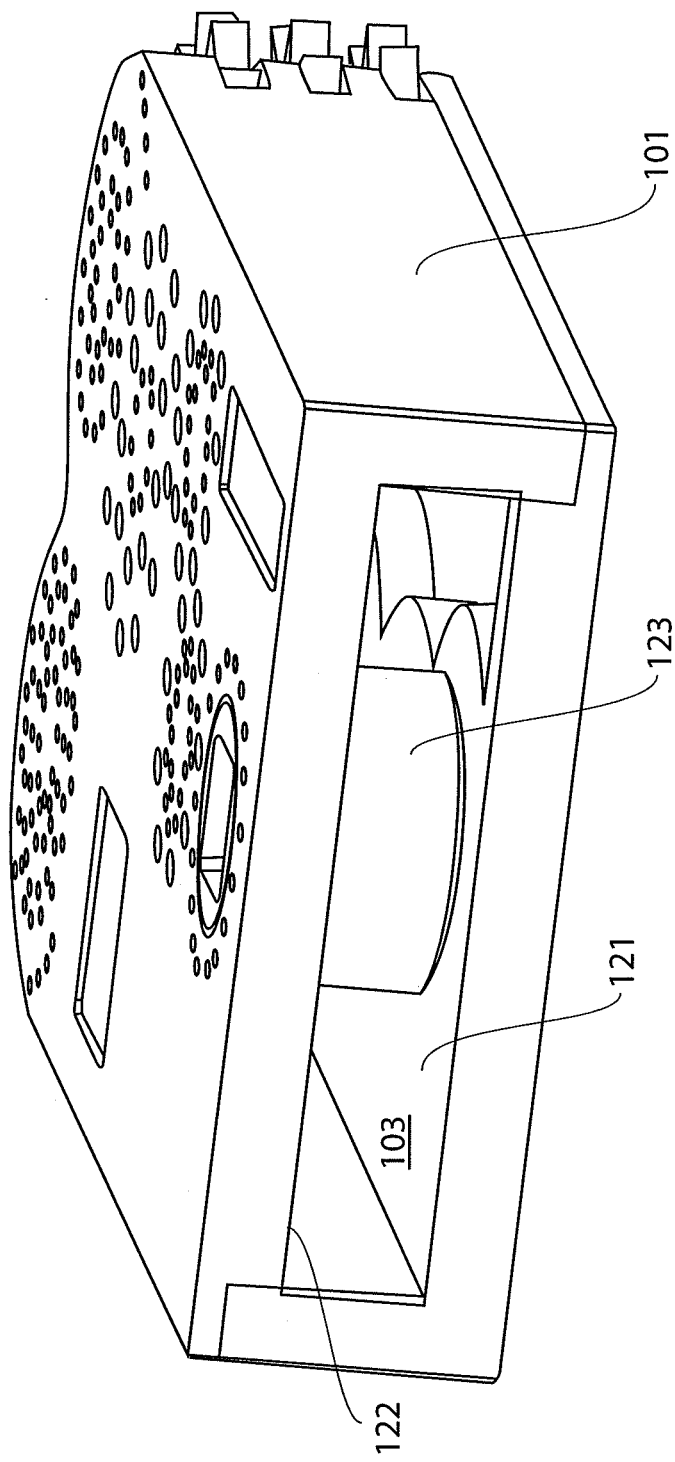
Figure 3:
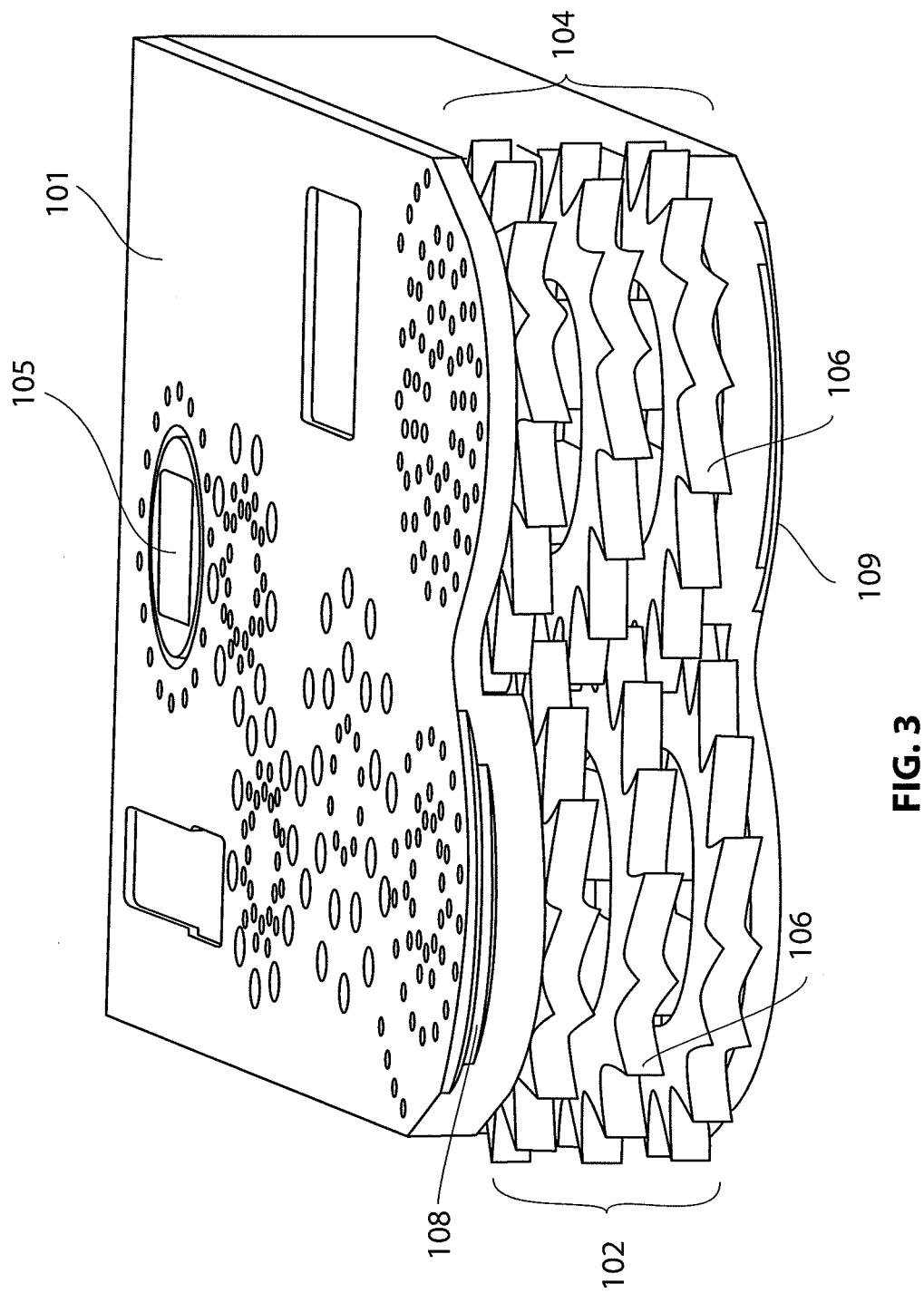

FIGS. 1-3 illustrate an exemplary embodiment of a working end of a tissue removal device, which can be fabricated wholly or in part by electrochemical fabrication techniques, such as those described or referenced herein. Tissue removal device working end 100 has a distal region "D" and proximal region "P," and includes housing 101 and blade stacks 102 and 104. Blade stacks 102 and 104 include a plurality of blades 102A-102C and 104A-104C, respectively. Three blades are shown in each stack, although the blade stacks can have one or more blades. Each of the blades includes a plurality of teeth 106 (see FIG. 3), some of which are shown projecting from housing 101 and configured to engage and process tissue. Processing tissue as used herein includes any of cutting tissue, shredding tissue, capturing tissue, any other manipulation of tissue as described herein, or any combination thereof. The working end of the device generally has a length L, height H, and width W. Housing 101 can have a variety of shapes or configurations, including a generally cylindrical shape.

In this embodiment both blade stacks are configured to rotate. The blades in blade stack 102 are configured to rotate in a direction opposite that of the blades in blade stack 104, as designated by the counterclockwise "CCW" and clockwise "CW" directions in FIG. 1. The oppositely rotating blades direct material, such as tissue, into an interior region of housing 101 (described in more detail below). In some embodiments, the blades can be made to be rotated in directions opposite to those indicated, e.g. to disengage from tissue if a jam occurs or to cause the device to be pulled distally into a body of tissue when given appropriate back side teeth configurations.

Housing 101 also includes a drive mechanism coupler 105, shown as a square hole or bore, which couples a drive train disposed in the housing to a drive mechanism disposed external to the housing. The drive mechanism, described in more detail below, drives the rotation of the drive train, which drives the rotation of the blades. The drive train disposed in the housing can also be considered part of the drive mechanism when viewed from the perspective of the blades. Drive mechanism coupler 105 translates a rotational force applied to the coupler by the drive mechanism (not shown) to the drive train disposed within housing 101.

FIG. 1 also shows release holes 111-115 which allow for removal of sacrificed material during formation of the working end.

FIG. 2 shows a perspective view of the proximal end of tissue removal device working end 100. Material directed into housing 101 by the rotating blades is directed into chamber 103, wherein it can be stored temporarily or directed further proximally, as described below. A first gear train cover 121 provides for a first surface of chamber 103, while a second gear train cover 122 provides a second surface of chamber 103. FIG. 2 also shows drive mechanism coupler cover 123.

In some embodiments in which the working end 100 includes a storage chamber, the chamber may remain open while in other embodiments it may be closed while in still other embodiments it may include a filter that only allows passage of items of a sufficiently small size to exit.

FIG. 3 shows a perspective view of the distal end of the working end 100. In this embodiment the blades in stack 102 are interdigitated with the blades in stack 104 (i.e. the blade ends are offset vertically along dimension H and have maximum radial extensions that overlap laterally along the width dimension W. The blades can be formed to be interdigitated by, e.g. if formed using a multi-layer, multi-material electrochemical fabrication technique, forming each blade in stack 102 in a different layer than each blade in stack 104. If during formation portions of separately moveable blade components overlap laterally, the overlapping blades should not just be formed on different layers but should be formed such an intermediate layer defines a vertical gap between them. For example, the bottom blade in stack 102 is shown formed in a layer beneath the layer in which the bottom blade in stack 104 is formed.

When manufacturing tissue removal devices of the various embodiments set forth herein using a multi-layer multi-material electrochemical fabrication process, it is generally beneficial if not necessary to maintain horizontal spacing of component features and widths of component dimensions remain above the minimum feature size. It is important that vertical gaps of appropriate size be formed between separately movable components that overlap in X-Y space (assuming the layers during formation are being stacked along the Z axis) so that they do not inadvertently bond together and to ensure that adequate pathways are provided to allow etching of sacrificial material to occur. For example, it is generally important that gaps exist between a gear element (e.g. a tooth) in a first gear tier and a second gear tier so that the overlapping teeth of adjacent gears do not bond together. It is also generally important to form gaps between components that move relative to one another (e.g., gears and gear covers, between blades and housing, etc.). In some embodiments the gaps formed between moving layers is between about 2 um and about 8 um.

In some embodiments, it is desired to define a shearing thickness as the gap between elements has they move past one another. Such gaps may be defined by layer thickness increments or multiples of such increments or by the intralayer spacing of elements as they move past one another. In some embodiments, shearing thickness of blades passing blades or blades moving past interdigitated fingers, or the like may be optimally set in the range of 2-100 microns or some other amount depending on the viscosity or other parameters of the materials being encountered and what the interaction is to be (e.g. tearing, shredding, transporting, or the like). For example for shredding or tearing tissue, the gap may be in the range of 2-10 microns, or in some embodiments in the range of 4-6 microns.

Figure 4A:
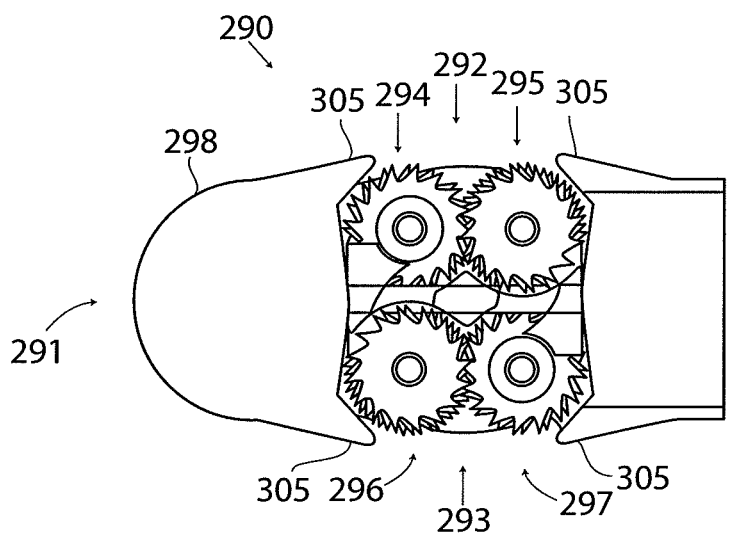
FIGS. 4A-4G illustrate exemplary embodiments of drive mechanisms which can power the drive trains in the working end of tissue removal devices.
Figure 4B:
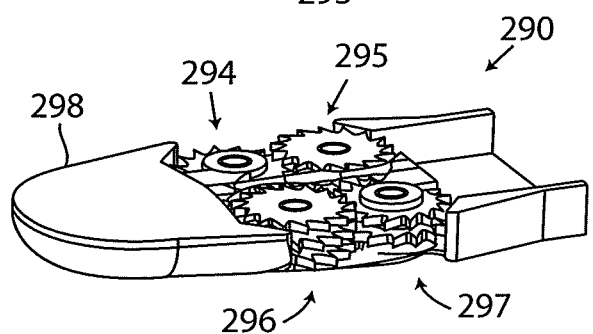
Figure 4C:
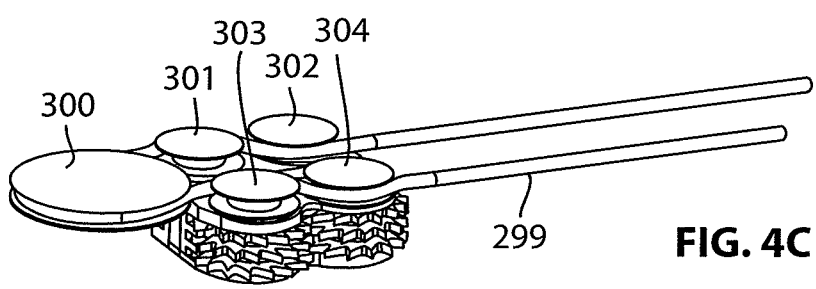
Figure 4D:
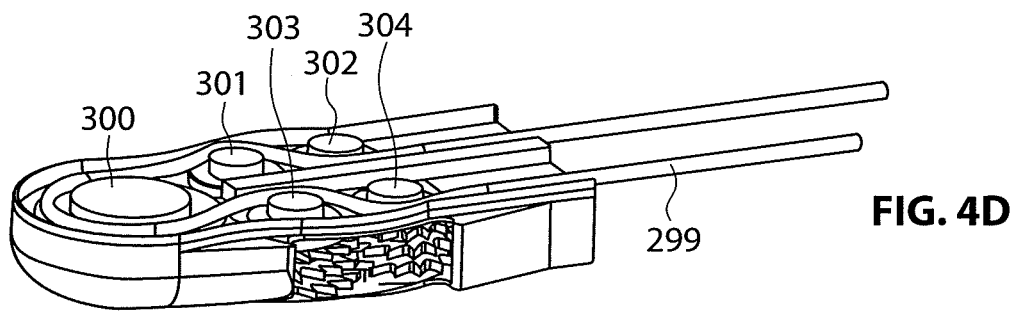
Figure 4E:
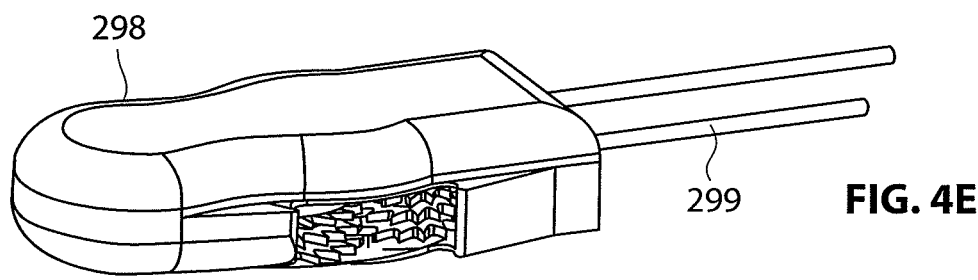
Figure 4F:
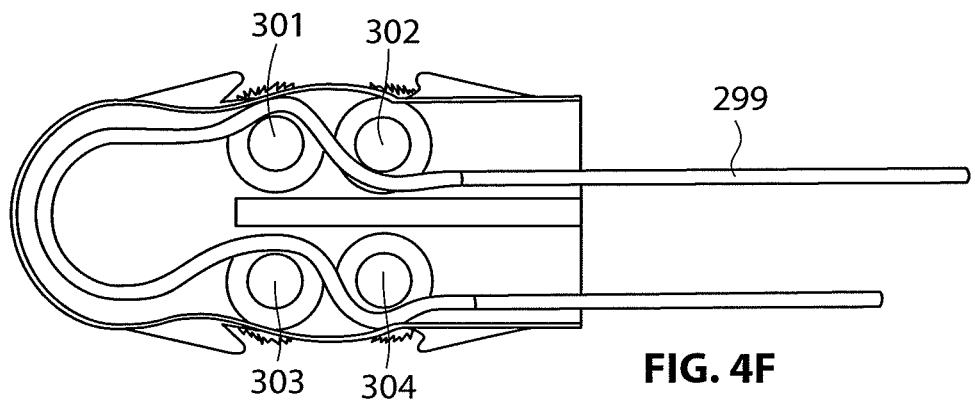
Figure 4G:
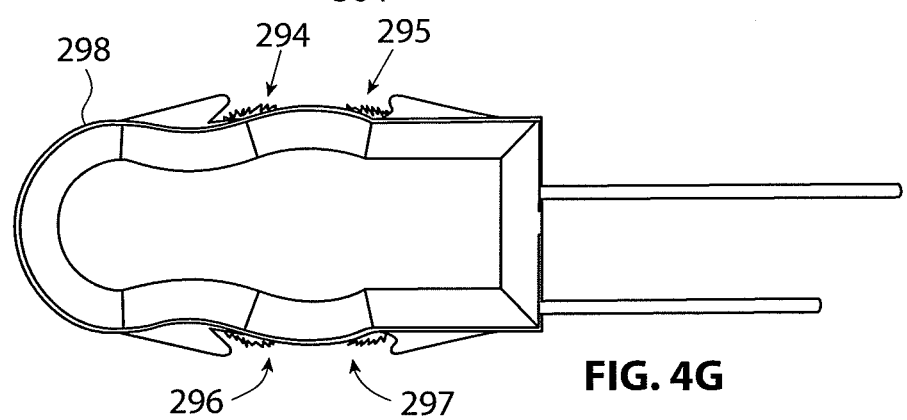

FIGS. 4A-4G illustrate an example a of a side tissue removal working end. FIG. 4A is a top sectional view with a top portion of the housing removed, which shows working end 290 comprising housing 298 and four tissue removal elements 294-297, which are shown as blade stacks. Blade stacks 294 and 295 process tissue along one side of the housing by directing tissue in the direction of arrow 292. Blade stacks 296 and 297 process tissue along a second side of the housing by directing tissue in the direction of arrow 293. As shown in FIGS. 4A-B, blade stacks 294 and 297 each have two blades, while blade stacks 295 and 296 each have three blades. FIG. 4C shows a perspective view without housing 298 illustrating the drive mechanism for the side tissue removal device 290. The drive mechanism includes belt 299, distal pulley 300, and side pulleys 301-304. The side pulleys are coupled to the blade stacks and rotation of the side pulleys rotates the blade stacks. The belt is disposed through side pulleys 301 and 302 and around distal pulley 300 before returning through side pulleys 303 and 304. Actuating of belt 299 therefore activates all four blade stacks. In some embodiments the belt is a nitinol wire, but can be any other suitable material. FIG. 4D is a view with the top portion of the housing removed to show the internal drive mechanism. FIG. 4E shows the same view with the top on the housing. FIGS. 4F and 4G show top views of the working end shown in FIGS. 4D and 4E, respectively. Vacuum, irrigation, or a combination of the two may be used to send extracted tissue from the interior of the working end, proximally to a storage reservoir (e.g. within the working end or located outside the body of the patient on which a procedure is being performed).

Figure 5A:
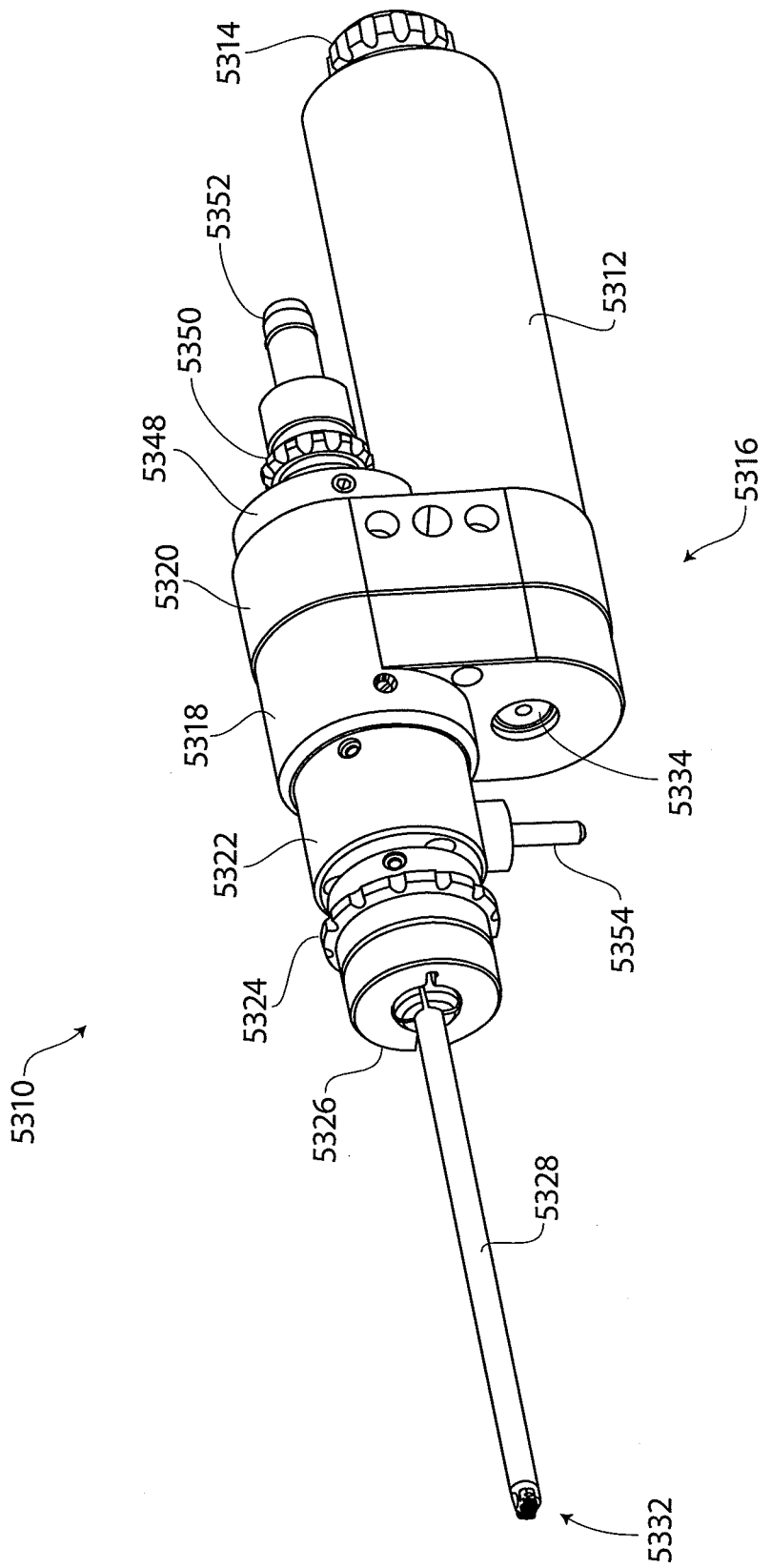
FIGS. 5A-5C show another exemplary embodiment of a tissue removal device.
Figure 5B:
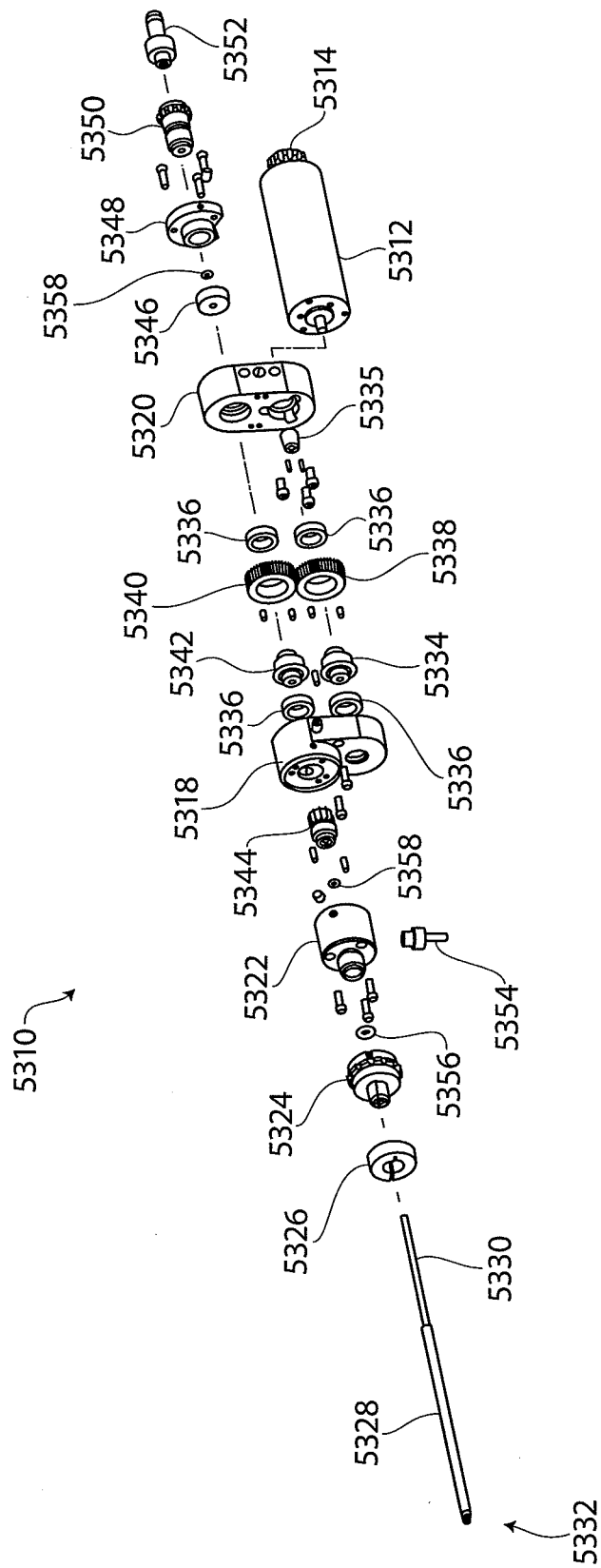
Figure 5C:
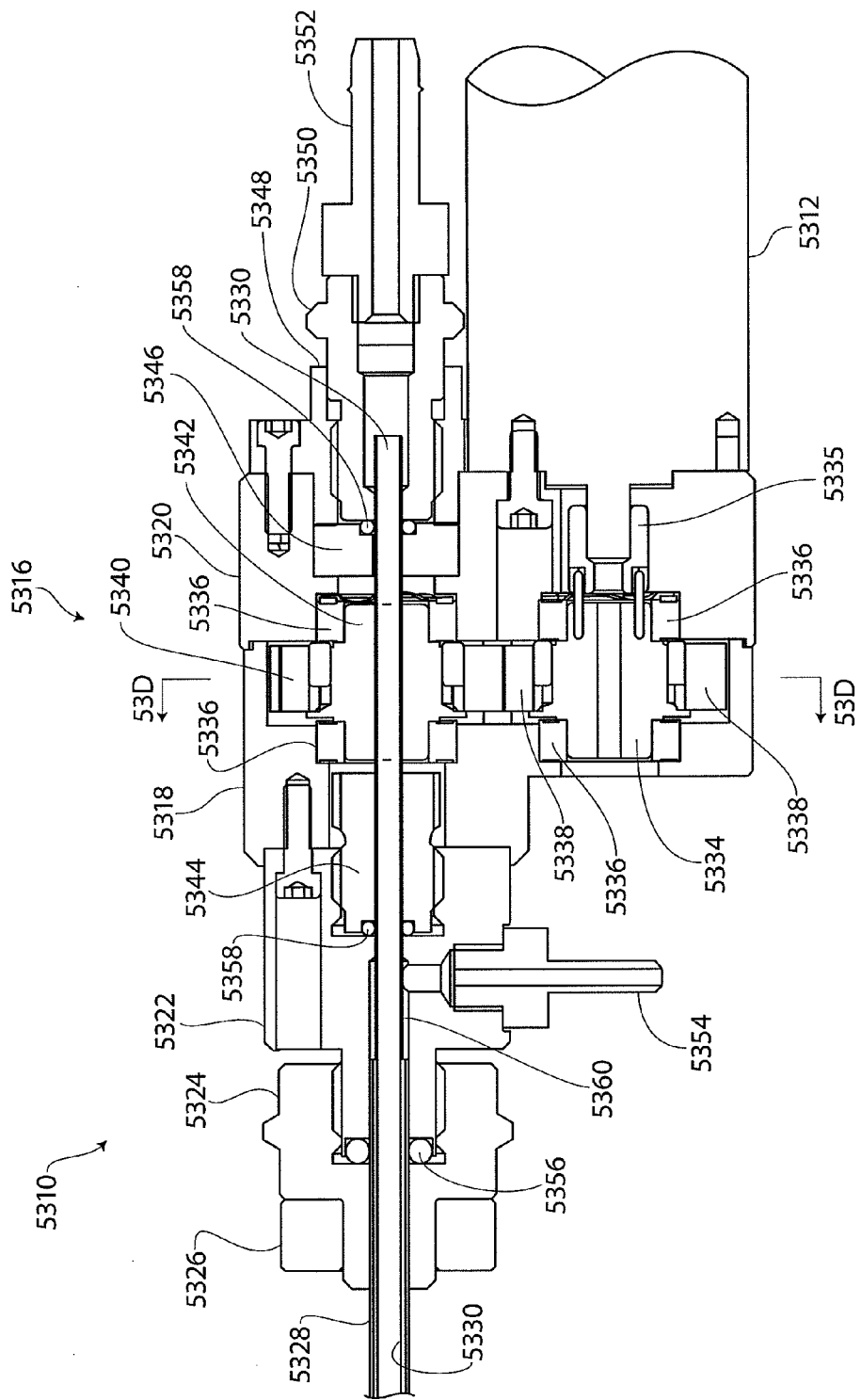

FIGS. 5A-5C show another exemplary embodiment of a tissue removal device. Device 5310 may employ any of the cutting heads described herein, or other suitable cutting heads. In some embodiments, a double rotor shredding head is employed at the distal end of device 5310 to selectively debride tissue down to the cellular level.

In this exemplary embodiment, handheld device 5310 includes a stepper motor 5312 at its proximal end. In other embodiments, other types of electric, pneumatic or hydraulic motors, servos, or other prime movers may be used. The proximal end of motor 5312 may be provided with a manually turnable thumbwheel 5314, as shown. In this embodiment, the distal output end of motor 5312 is provided with a housing 5316, which is made up of a front cover 5318 and a rear cover 5320. Located distally from housing 5316 are an outer shaft housing 5322, an outer shaft lock seal 5324, and a support clamp 5326. A non-rotating, outer support tube 5328 extends from within the proximal end of device 5310 towards the distal end of the device. Within support tube 5328, a rotating drive tube 5330 (best seen in FIGS. 5B and 5C) also extends from within the proximal end of device 5310 towards the distal end of the device. The support tube 5328 and inner drive tube 5330 may collectively be referred to as an introducer. A cutter head assembly 5332, subsequently described in detail, is attached to the distal end of support tube 5328.

As best seen in FIG. 5B, other components of device 5310 include motor shaft drive axle 5334, motor dog 5335, four bearings 5336, drive gear 5338, driven gear 5340, inner drive shaft axle 5342, inner shaft lock seal 5344, vacuum gland disk 5346, vacuum seal lock housing 5348, vacuum seal lock 5350, vacuum hose barb 5352, irrigation fluid hose barb 5354, outer tube o-ring 5356, and two vacuum gland o-rings 5358. Various other pins, dowels, fasteners, set screws, ball detents, shims and wave disc springs are shown in the figures without reference numerals. As will be appreciated by those skilled in this art, these non-referenced components serve to align, retain and ensure the proper functioning of the other components of exemplary device 5310.

The two rotors of cutter head assembly 5332 located at the distal end of device 5310 are driven by motor 5312 through drive tube 5330 and other drive components of device 5310, as will now be described in more detail. As best seen in FIGS. 5B and 5C, a motor dog 5335 is attached to the output shaft of motor 5312. Motor dog 5335 is coupled to motor shaft drive axle 5334, which is rotatably mounted in housing 5316 with two bearings 5336. Drive gear 5338 is rigidly fixed to motor shaft drive axle 5334, and drives driven gear 5340. Driven gear 5340 is rigidly fixed to inner drive shaft axle 5342, which is rotatably mounted in housing 5316 with two bearings 5336. Inner rotating drive tube 5330 passes through the center of inner drive shaft axle 5342 and is rotatably fixed thereto. Drive tube 5330 extends from the proximal end of device 5310 to the distal end of the device through the non-rotating outer support tube 5328. The distal end of drive tube 5330 (or a separate tube 5330' attached thereto) is provided with crown teeth around its periphery, as shown in FIGS. 6B and 6C, for meshing with drive gear 5410. As drive tube 5330 is rotated about a longitudinal axis of device 5310 by motor 5312 through the above-described drive train components, it drives drive gear 5410 about an axis that is perpendicular to the longitudinal axis, as can be appreciated by viewing FIG. 6. Drive gear 5410 in turn drives other components of the cutter head assembly, and as is subsequently described in more detail.

In some embodiments motor 5312 is provided with feedback control for rotational velocity and torque. These two parameters can be used for controlling and monitoring changes in rotational velocity and the torque load. For measuring rotational velocity, an encoder may be located at one or more of the cutter rotors, at the drive motor, or at another location along the drive train between the drive motor and cutter rotors. In some embodiments, the encoder is located at or close to the rotors to avoid backlash associated with the drive train, thereby making the velocity monitoring more responsive and accurate. Encoder technologies that may be used include optical, resistive, capacitive and/or inductive measurement. To sense torque load, one or more strain gages may be located at the cutter rotors, at the drive motor, or at another location along the drive train between the drive motor and cutter rotors. Torque load may also be sensed by monitoring the current being drawn by the motor. By sensing changes in velocity and/or torque, a controller associated with device 5310 can determine that the cutter rotors are passing from one tissue type to another and take appropriate action. For example, the controller can sense when the cutter elements are passing from soft to hard tissue, from hard to medium density tissue, or from a cutting state to non-cutting state. In response to these changes, the controller and/or device 5310 can provide audio, visual and/or tactile feedback to the surgeon. In some embodiments, the controller can change the velocity, direction or stop cutter rotors from rotating in response to velocity and/or torque feedback. In one embodiment of the invention, a typical cutting rotor speed is on the order of 100 to 20,000 rotations per minute, and a typical torque load is on the order of 0.25 to 150 mN-meter. Other sensors, such as a pressure sensor or strain sensor located at the distal tip of device 5310, may also be utilized to provide feedback that tissue cutting elements are moving from one tissue type to another.

In some embodiments, an impendence sensor may be located at the distal tip of the device, to sense different tissue types or conditions, and provide corresponding feedback for tissue cutting control when the tissue being cut by the cutter head changes. Such a pressure sensor feedback control arrangement can be used with types of cutting devices other than those disclosed herein.

Referring now to FIG. 5C, irrigation fluid hose barb 5354 is provided on the lower side of outer shaft housing 5322 of exemplary device 5310. Hose barb 5354, or a similar fluid line coupling, may be connected to a supply of irrigation fluid. The lumen of hose barb 5354 is in fluid communication with an internal irrigation fluid cavity 5360. Fluid cavity 5360 surrounds internal drive tube 5330, and is bounded on its proximal end by o-ring seal 5358 around drive tube 5330. Fluid cavity 5360 is bounded on its distal end by o-ring seal 5356 around outer support tube 5328. This arrangement allows drive tube 5330 to rotate, but constrains irrigation fluid delivered from hose barb 5354 to travel only through the annular space defined by the outer surface of drive tube 5330 and the inner surface of support tube 5328. Irrigation fluid may thus flow distally through the annular space to the distal end of device 5310.

As shown in FIG. 6B, one or more drive aligner rings 5412 may be provided between outer support tube 5328 and inner drive tube 5330 along their lengths to support drive tube 5330 as it rotates. In order to allow the flow of irrigation fluid between the tubes 5328 and 5330, rings 5412 may be provided with one or more channels 5414 as shown. When the distal flow of irrigation fluid reaches the cutter head assembly 5332, it continues to flow distally into lug 5416. To enable the fluid flow, lug 5416 is provided with fluid channels 5418 located along the outer walls of its central bore, as best seen in FIG. 6C. In this embodiments, irrigation fluid passes distally between inner drive tube 5330 and lug 5416 through channels 5418 (only one channel shown in FIG. 6C). Irrigation fluid flowing distally through channels 5418 may be directed toward the outside portions of cutting elements. In this embodiment, the outside portions of cutting elements are rotating distally, away from the fluid flow, while the inside portions of cutting elements are rotating proximally, toward the center of lug 5416 and drive tube 5330.

In some embodiments, the irrigation fluid serves multiple functions. The irrigation fluid can serve to lubricate the cutting elements, drive gears, journal bearings and other components as the parts rotate. The irrigation fluid can also serve to cool the cutting elements and/or the tissue being cut, absorbing heat and carrying it away as the irrigation fluid is removed from the patient. The fluid can serve to flush tissue particles from the moving parts to prevent them from becoming clogged. The fluid can also serve to carry away the tissue portions being cut and remove them from the target tissue site. In some embodiments, the fluid comprises a saline solution. In some embodiments, the irrigation fluid is discharged from the cutting device and may be removed from the target tissue site with other, traditional aspiration means. With the current exemplary cutting device 5310, however, the irrigation fluid and/or other bodily fluids may be removed from the target tissue site by the cutting device 5310, as will now be described in detail.

As previously described, irrigation fluid may be delivered to cutting elements and/or a target tissue site through device 5310. Exemplary device 5310 is also constructed to remove the irrigation fluid and tissue portions cut from the target tissue site through the shaft of device 5310. As can be appreciated by viewing FIG. 7F, the two interleaving stacks of cutting elements, also referred to as rotors 5610 and 5612, have an overlapping section 5614 in the center of cutter head assembly 5332. The two rotors 5610 and 5612 may be rotated in opposite directions such that each rotor engages target tissue and pulls it towards the central overlapping section 5614. In overlapping section 5614, the tissue is shredded into small pieces by the interdigitated cutting elements, as is subsequently described in more detail. The small tissue portions are generally propelled in a proximal direction by rotors 5610 and 5612, away from the target tissue site and into the cutter head assembly 5332. As can be appreciated by viewing FIG. 7F, the shredded tissue portions emerge from rotors 5610 and 5612 substantially along the central axis of lug 5416 (and therefore also the central axis of drive tube 5330. With sufficient irrigation fluid being supplied to the tissue cutting area, and sufficient aspiration being provided from the proximal end of the device, irrigation fluid around rotors 5610 and 5612 carries the cut tissue particles proximally down the center of drive tube 5330. As shown in FIG. 5C, the proximal end of drive tube 5330 is in fluid communication with hose barb 5352 located at the proximal end of device 5310. A traditional aspiration device or other suction source may be attached to device 5310 through hose barb 5352 or other suitable fluid coupling to collect the spent irrigation fluid and cut tissue portions.

In some embodiments, the cut tissues portions emerging from hose barb 5352 may be collected for testing. The tissue portions may be separated from the irrigation fluid, such as by centrifugal force, settling and/or filtering. The tissue portions may be measured to precisely determine the mass and/or volume of tissue removed. The pathology of some or all of the tissue portions may also be determined. In some embodiments, the above testing may be performed during a surgical procedure so that results of the testing may be used to affect additional stages of the procedure.

According to aspects of the invention, the inside diameter of drive tube 5330 may be much larger than the maximum dimension of the tissue portions traveling through it. In some embodiments, the maximum tissue dimension is less than about 2 mm across. In one exemplary embodiment, the inside diameter of drive tube 5330 is about 3 mm, the outside diameter of the support tube 5328 is about 5.6 mm, and the maximum dimension of the tissue portions is about 150 microns. In another exemplary embodiment, the inside diameter of drive tube 5330 is about 1.5 mm, the outside diameter of the support tube 5328 is about 2.8 mm, and the maximum dimension of the tissue portions is about 75 microns. In other embodiments, the inside diameter of drive tube 5330 is between about 3 mm and about 6 mm. In some embodiments, the maximum dimension of the tissue portions is at least one order of magnitude less than a diameter of the tissue removal lumen. In other embodiments, the maximum dimension of the tissue portions is at least twenty times less than a diameter of the tissue removal lumen. In some embodiments, the maximum dimension of the tissue portions is less than about 100 microns. In other embodiments, the maximum dimension of the tissue portions is about 2 microns.

Figure 6A:
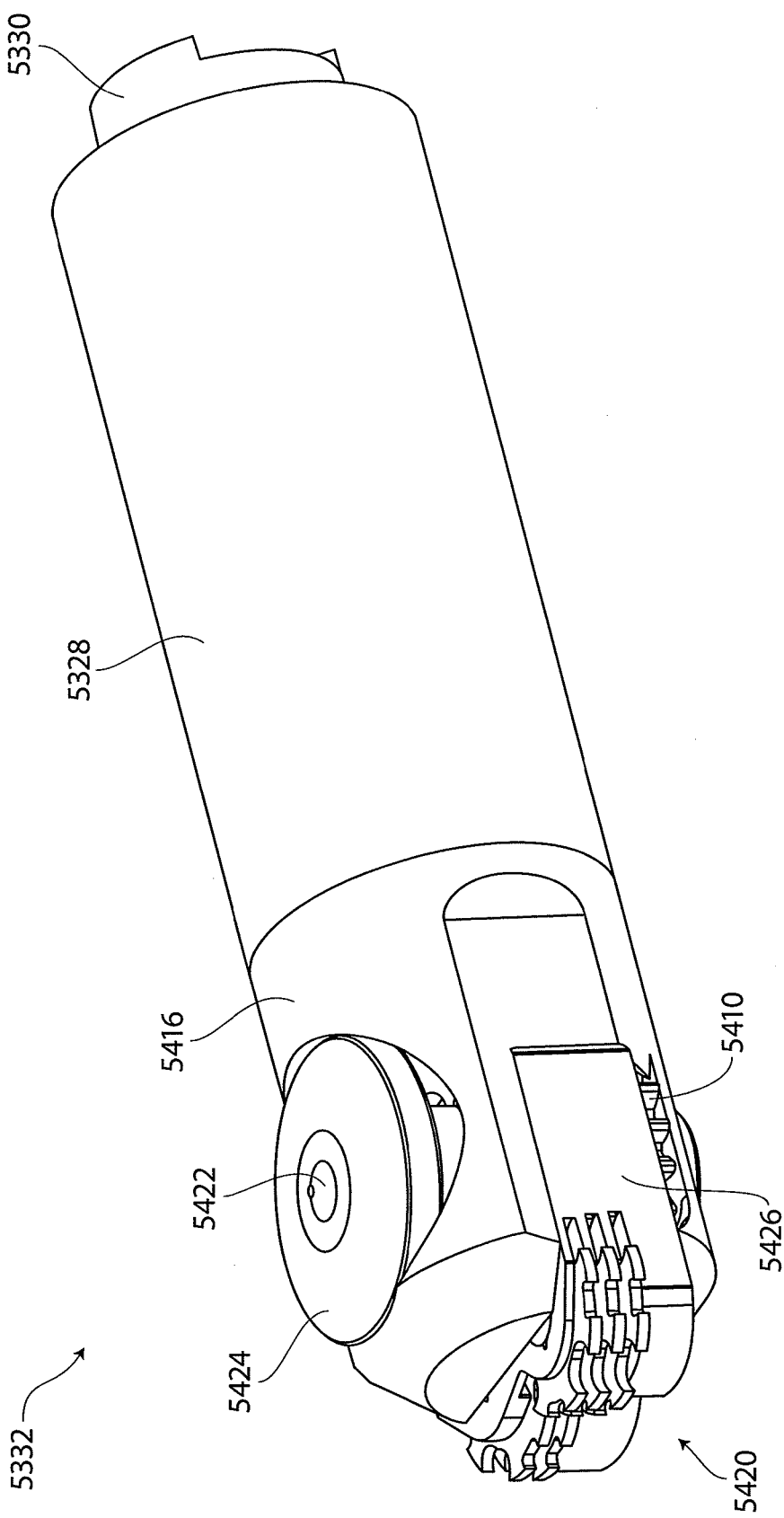
FIGS. 6A-6C show an exemplary cutter head assembly 5332 that may be used with debriding device 5310, shown in FIGS. 5A-5C.
Figure 6B:
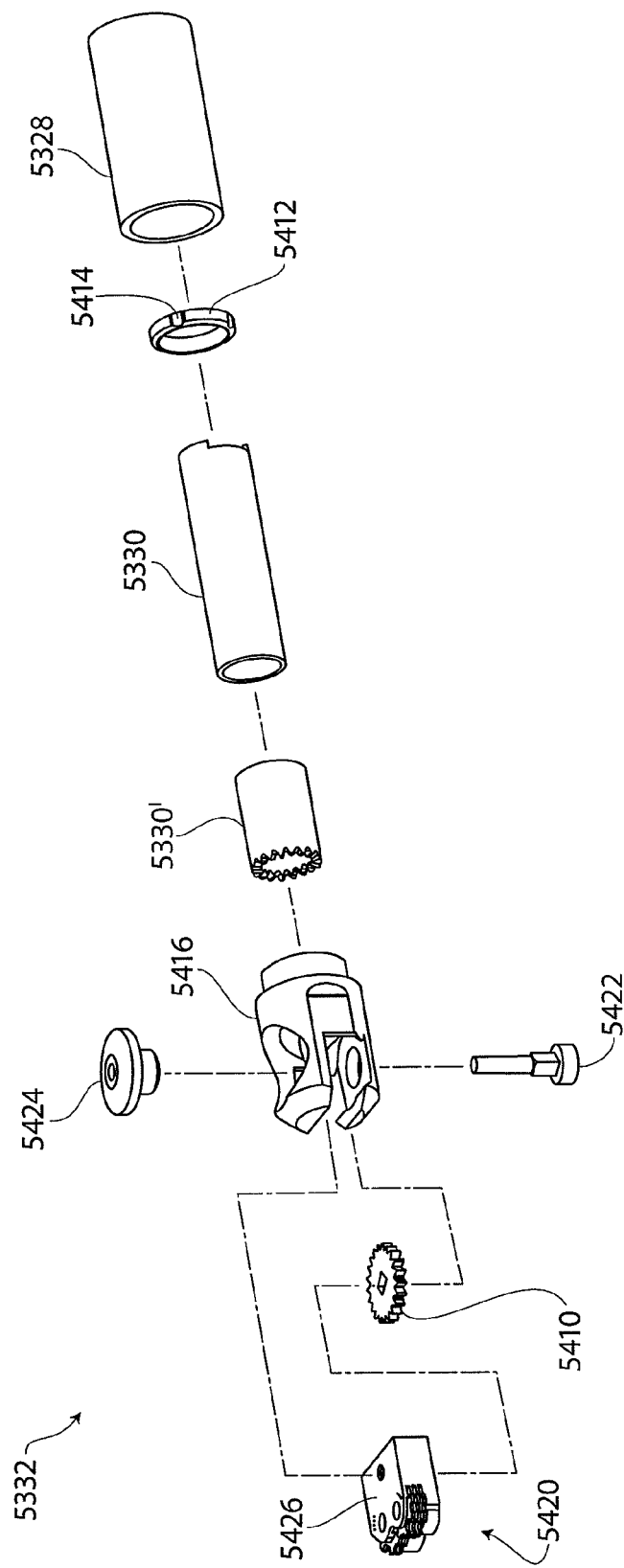
Figure 6C:
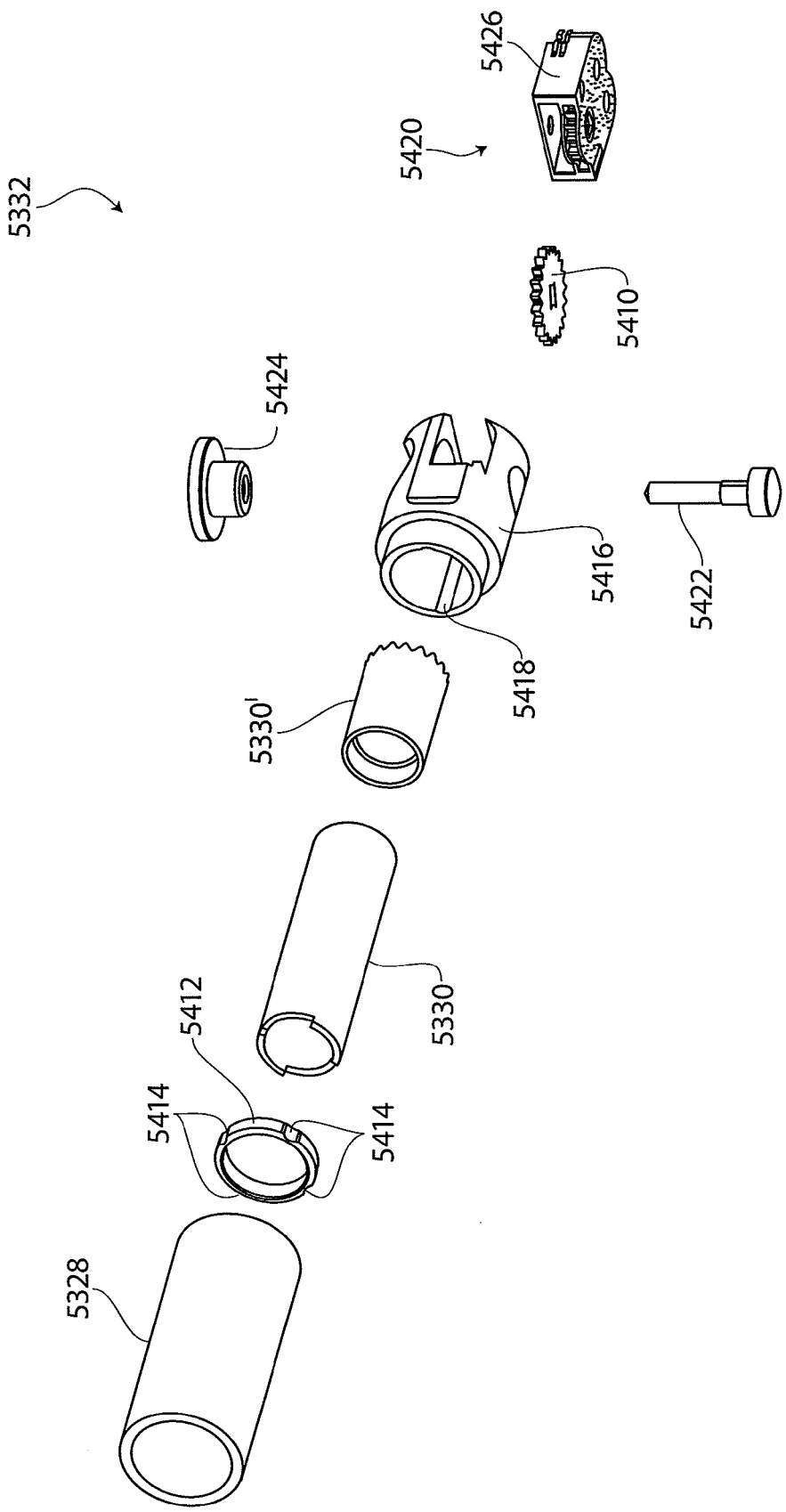

Referring now to FIGS. 6A-6C, an exemplary cutter head assembly 5332 is described in more detail. Cutter head assembly 5332 may be used with debriding device 5310, shown in FIGS. 6A-6C. As best seen in FIG. 6B, cutter head assembly 5332 includes lug 5416, drive gear 5410, rotor housing assembly 5420, aligner pin 5422, and aligner cap 5424. Lug 5416 is provided with a cutout on its distal end for receiving rotor housing assembly 5420. Beneath the rotor housing cutout, lug 5416 has a circular recess for receiving drive gear 5410. A bore is provided in the bottom of lug 5416 for receiving the head of aligner pin 5422. When cutter head 5332 is assembled, the shank of aligner pin 5422 passes through the bore of lug 5416, through a square aperture in the center of drive gear 5410, through a bore in the proximal end of rotor housing assembly 5420, and into a large diameter bore through the top of lug 5416. Aligner cap 5424 is received with the large diameter bore in the top of lug 5416, and is fastened to aligner pin 5422 by a press fit, weld, threads, a separate fastener, or other suitable means. In this assembled arrangement, pin 5422 and cap 5424 retain rotor housing 5426 from moving longitudinally relative to the central axis of the instrument, and rotor housing 5426 and drive gear 5410 retain pin 5422 and cap 5424 from moving radially relative to the central axis of the instrument. Pin 5422 and cap 5424 spin together as a unit relative to lug 5416, and serve to align drive gear with the distal end of drive tube 5330', as previously described. Pin 5422 also serves to transmit torque from drive gear 5410 to gear 5616, which resides inside the rotor housing directly above drive gear 5410. Lug bearing 5416 forms the base of cutter head assembly 5332, shown in FIGS. 6A-6C. As subsequently described in further detail, various different cutter heads may alternately be inserted into and secured within the slot shaped opening in the distal end of the lug bearing.

Figure 7A:
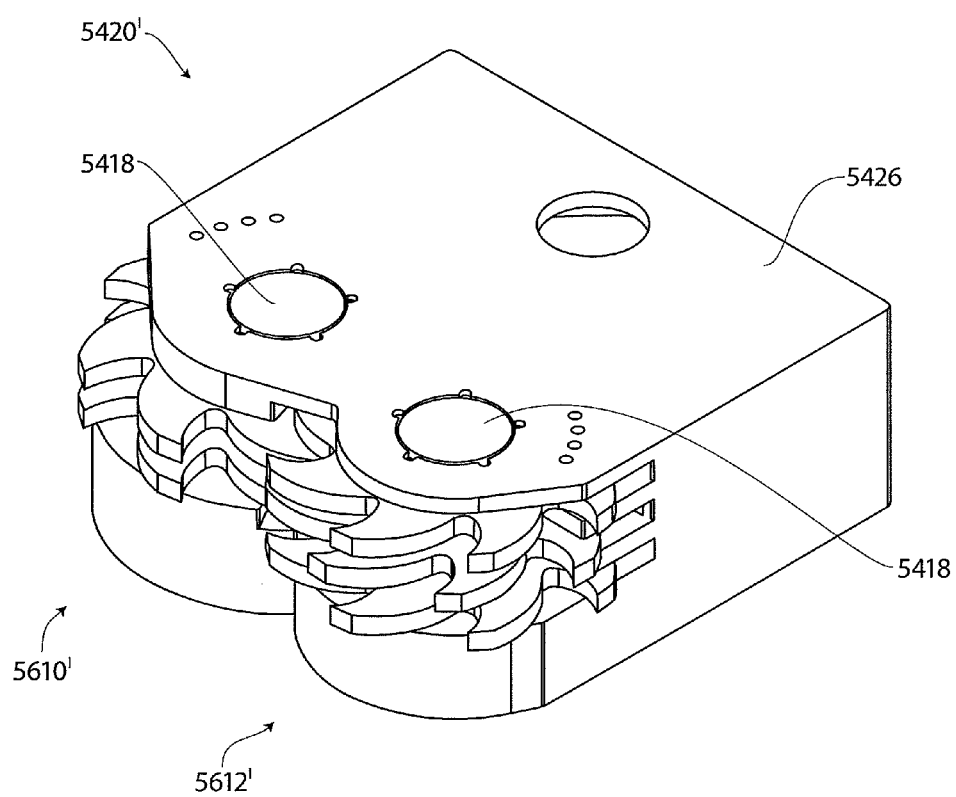

FIGS. 7A-7F show further details of an exemplary rotor housing assembly 5420'. Assembly 5420' is constructed and operates in a manner similar to assembly 5420 as previously described in reference to FIGS. 6A-6C, but has a different blade configuration. As shown in FIG. 7A, rotor housing assembly 5420' includes a pair of rotors 5610' and 5612', each rotatably mounted in rotor housing 5426 by an axle 5618. In this embodiment, rotors 5610' and 5612' are configured to rotate in opposite directions to draw tissue into a center, overlapping region where the tissue is shredded.

Figure 7B:
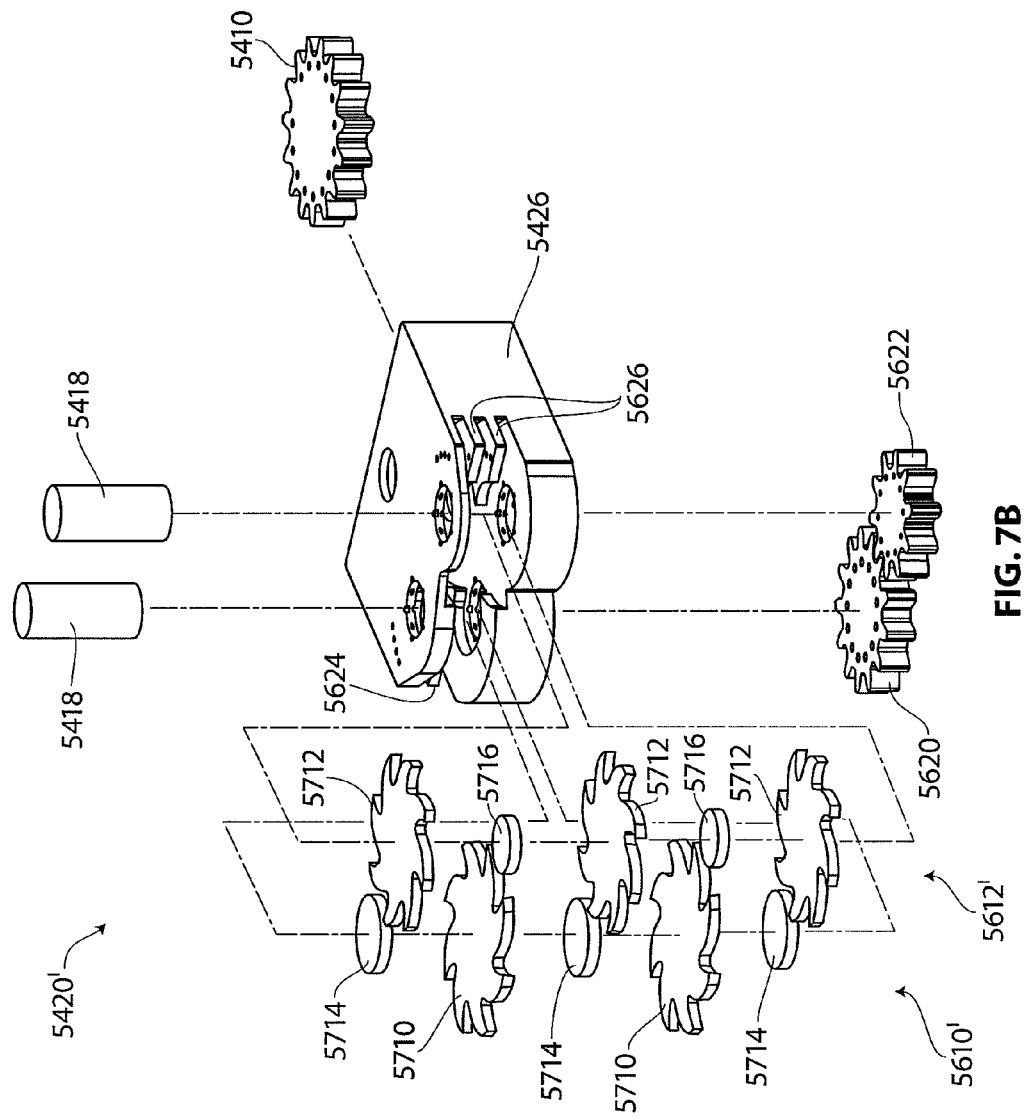
Figure 7C:
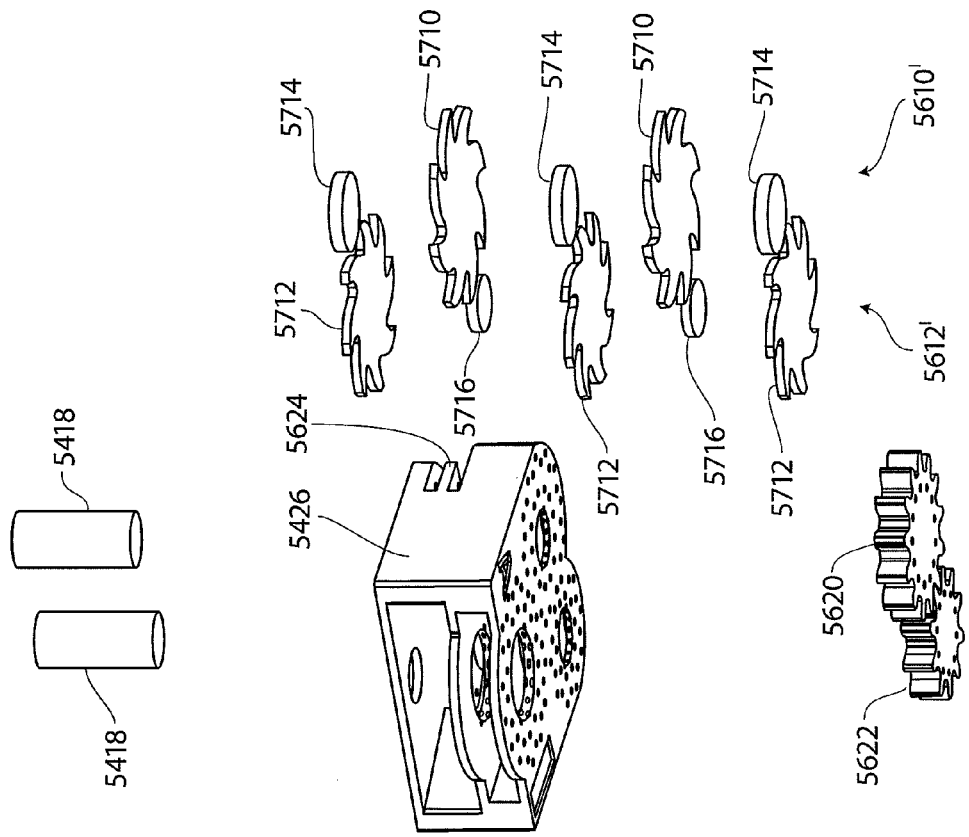
Figure 7E:
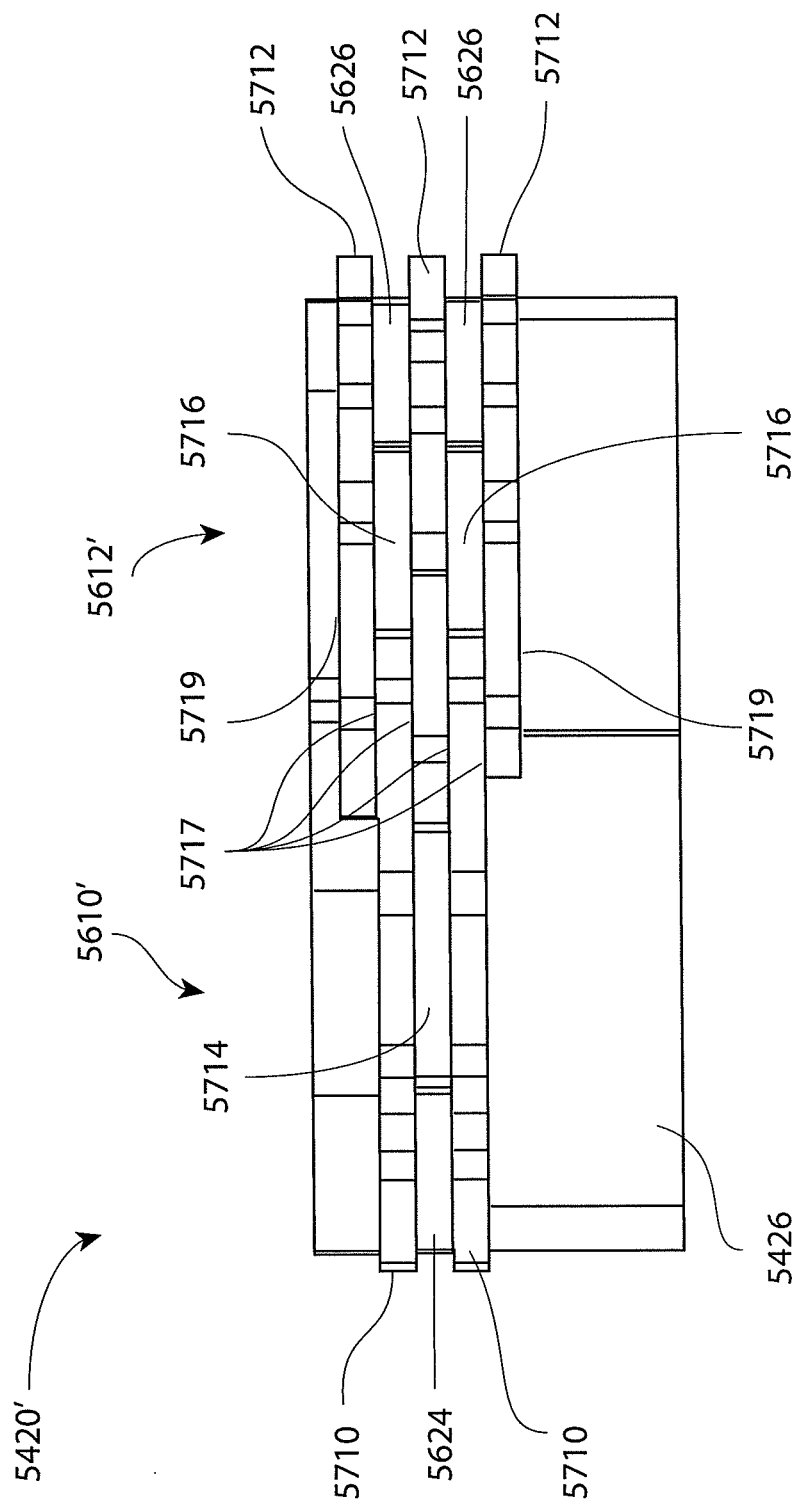

Referring to FIGS. 7B and 7C, the components of rotor housing assembly 5420' are shown. Assembly 5420' includes housing 5426, a pair of axles 5418, and gears 5410, 5620 and 5622, as previously described. Rotor 5610' includes two blades 5710 interspersed with three spacer rings 5714 on first axle 5418. Rotor 5612' includes three blades 5712 interspersed with two spacer rings 5716 on second axle 5418.

It should be noted that while rotor housing assembly 5420' is shown in an exploded format for clarity in FIGS. 7B and 7C, suggesting that the components are fabricated separately and then assembled using traditional assembly processes, this may or may not be the case, depending on the embodiment. In some embodiments, rotor assembly 5420' is assembled this way. In other embodiments, assembly 5420' may be built in layers, such as by using a MEMS fabrication processes. For example, after portions of housing 5426 and gears 5410, 5620 and 5622 are built up in layers, bottom blade 5712, bottom spacer 5714, and housing fin 5624 are formed together in one or more layers. Following this layer, bottom blade 5710, bottom spacer 5716, and bottom housing fin 5626 may be formed together in one or more layers. The process may be repeated until the entire rotors 5610' and 5612' and surrounding components are formed. A thin sacrificial layer may be formed between adjacent layers of components to separate the components from one layer from components of adjacent layers. Sacrificial material may also be formed in portions of each non-sacrificial layer to separate components on that layer, create desired voids in the finished assembly, and to provide a substrate for forming components in subsequent layers above. With such a fabrication technique, rotor 5610' may be formed as a single unitary structure interleaved with portions of rotor housing 5426, rather than separate components (i.e. axle 5418, spacers 5714, blades 5710, and gear 5620.) Similarly, rotor 5612' may be formed as a single unitary structure interleaved with portions of rotor housing 5426, rather than separate components (i.e. axle 5418, blades 5712, spacers 5716, and gear 5622.) In some embodiments, combinations of fabrication and assembly techniques may be used to create the rotor housing and/or cutter head assemblies.

Referring to the top view shown in FIG. 7D, it can be seen that in this embodiment the axle 5418 of rotor 5612' is more distally located than axle 5418 of rotor 5610'. It can also be seen that while a top plate portion of rotor housing 5426 covers most of rotor blades 5710 and 5712, the blades protrude less from a middle and bottom plate portion of housing 5426. Further details of protruding blades and rotor characteristics are subsequently discussed in reference to FIG. 7F.

A front or distal end view is shown in FIG. 7G. As depicted in FIG. 7G, very small gaps or interference fits 5717 between overlapping blades 5710 and 5712 are desirable in some embodiments. Similarly, very small gaps or interference fits 5719 between blades 5712 and adjacent portions of rotor housing 5426 are desirable in some embodiments, as will be subsequently described in more detail.

Referring to the cross-sectional plan view of FIG. 7F, the bottom two blades 5712 of rotor 5612' and the bottom blade 5710 of rotor 5610' are shown. As shown, blades 5710 have a larger outer diameter than that of blades 5712. But because axle 5418 of rotor 5612' is located more distally than axle 5418 of rotor 5610', blades 5712 protrude more distally from the bottom of rotor housing 5426 than do blades 5710 of rotor 5610'. It can also be seen that teeth 5718 and associated troughs 5720 of blades 5712 are configured to be rotationally out of phase with those of other blades 5712 of rotor 5612'. As will subsequently be discussed in more detail, this arrangement can tune rotors 5612 to selective cut certain types of tissue and avoid cutting other types of tissue.

Various rotor gaps can be seen in FIG. 7F. For example, gap 5722 is shown between the tips of blade teeth 5718 of rotor 5612' and spacer ring 5714/axle 5418 of opposing rotor 5610'. Gap 5724 is also shown, between the tips of blade teeth 5718 of rotor 5612' and the adjacent portion of housing 5426. Gap 5726 is also shown, between spacer ring 5714/axle 5418 of rotor 5610' and the adjacent portion of housing 5426. In some embodiments, it is desirable to keep gaps 5722, 5724 and 5726 very small, to ensure that tissue portions/particles that pass through rotors 5610' and 5612' are first cut to a very small size, and to avoid jamming or clogging rotors 5610' and 5612'. In some embodiments, these gaps are fabricated as small interferences between the adjacent parts so that when the rotors are first rotated, the adjacent parts hit each other and wear down or burnish each other. In this manner, after a break in period, smaller interference or zero clearance fits are created between the adjacent moving parts. Gap distances that applicants believe are advantageous include less than about 20 microns, less than about 10 microns, less than about 5 microns, less than about 1 micron, substantially zero, an initial interference fit of at least 2 microns, and an initial interference fit of about 5 microns.

In operation, the cutter elements of rotor housing assembly shown in FIGS. 7A-7F serve to grab tissue from a target source, draw the tissue towards a central region between the blades, cut the tissue from the source, and morcellate the tissue in small pieces for transport away from the body. In other embodiments, separate cutter elements may be used for these various functions. For example, one blade or blades may be used to cut tissue from the source, while another blade or set of blades may be used to morcellate the cut tissue.

Components of cutter head assembly 5332, including rotor housing assemblies 5420 and 5420', may be fabricated using processes such as laser cutting/machining, photo chemical machining (PCM), Swiss screw, electro-discharge machining (EDM), electroforming and/or other processes for fabricating small parts. Wafer manufacturing processes may be used to produce high precision micro parts, such as EFAB, X-ray LIGA (Lithography, Electroplating, and Molding), and/or UV LIGA. An electrochemical fabrication technique for forming three-dimensional structures from a plurality of adhered layers is being commercially pursued by applicant Microfabrica® Inc. (formerly MEMGen Corporation) of Van Nuys, Calif. under the name EFAB®. Such a technique may be advantageously used to fabricate components described herein, particularly rotors and associated components.

In some embodiments, the shredder's ability to selectively remove tissue is attributed to the protrusion of the rotating cutters from the housing and the design of a tooth pitch (space between the tips of adjacent teeth) of each rotor. In some embodiments, the protrusion sets the depth of the inward cut for the tips of the rotor. This inward depth controls the thickness of tissue being removed. The tooth pitch or number of teeth circumferentially about the rotor diameter provides an opening for individual tissue fibers and/or fiber bundles to be hooked, tensioned and drawn between the cutters.

From the point of view of the selected tissue, the tooth pitch and protrusion may be designed to grasp the smallest fibers or fiber bundles that are to be removed. From the point of view of the non-selected tissue, the tooth pitch may be many times smaller than the fiber or fiber bundle, and the protrusion may also be equally smaller than the fiber/bundle diameter.

As previously described, FIG. 7D shows the exemplary protrusion of blades 5710 and 5712 as viewed from the top of a rotor housing assembly 5420'. In some embodiments, the protrusion is more exposed on the top side than the bottom. In other embodiments, the cutter device has the same protrusion for both sides. Biasing the protrusion more on one side than the other can provide advantages such as cutting/shredding directionality and/or additional safety. Blade protrusion distances that applicants believe are advantageous include less than about 100 microns, less than about 10 microns, substantially flush with the housing, recessed a minimum of about 5 microns, and recessed a minimum of about 10 microns.

Tooth pitch is the distance from one tooth tip to the next tooth tip along an imaginary circle circumscribing the outer circumference of the blade. The trough diameter or depth generally is the distance between the tooth tip and the low point between the tooth tips. In many embodiments, the trough is a critical geometry component that enables tissue selectivity. Additionally, the trough opening (i.e. the distance from tooth tip to the tooth back of an adjoining tooth) can determine the size of the "window" for capturing a fiber or fiber bundle diameter.

In some embodiments, the target tissue being cut is hydrated and generally has a nominal fiber diameter of about 6 to about 9 microns. In some embodiments, the target tissue being cut is dry and generally has a nominal fiber diameter of about 5 to about 6 microns. In some embodiments, the tissue fibers are connected together in bundles having a nominal diameter of about 250 microns.

Typical dimensions in some embodiments include:
Housing diameter: 6 mm or less
Blade diameter range: 0.75 mm to 4 mm
Tip to Tip range: 0.2 mm to 1 mm
Trough diameter range: 2 microns to 0.5 mm
Blade protrusion range: 2 microns to 2 mm The tip to tip distance is typically at least two times the trough diameter for hook type teeth.

The tissue cutting devices disclosed herein may be configured for use in a variety of procedures. An example of a cardiac application is using the inventive devices to selectively remove endocardium, with the cutting device configured to leave the underlying myocardium uncut. An example of a tissue removing application involving the esophagus includes selectively removing mucosa, leaving the submucosa. Such a therapy would be useful for treating Barrett's disease. Examples in the spinal area include selectively removing flavum, with the cutting device configured to stop removing tissue when dura is reached, leaving the dura intact. Selective removal of flavum but not nerve root is another embodiment. A cutting device constructed according to aspects of the invention can also be configured to remove flavum without cutting bone. In this embodiment, the rotor velocity could be changed and/or the cutting elements could be changed after the flavum is removed such that some bone tissue could then be removed. Examples in the neurovascular area include selectively removing cancerous tissue while not cutting adjacent blood vessel tissue or nerve tissue. In the rheumatology field, tears in labral target tissue may be selectively removed while preserving adjacent non-target tissue, such as in the hips, shoulders, knees, ankles, and small joints. In some embodiments, small teeth on the rotors can interact with micron scale fibers of cartilage, removing tissue in a precise way, much like precision machining of materials that are harder than tissue. Other target tissues that may be selectively removed by the inventive devices and methods described herein include cartilage, which tends to be of a medium density, periosteum, stones, calcium deposits, calcified tissue, cancellous bone, cortical bone, plaque, thrombi, blood clots, and emboli.

It can be appreciated by those skilled in the art of tissue removal that soft tissue is much more difficult to remove in a small quantities and/or in a precise way than harder tissue such as bone that may be grinded or sculpted, since soft tissue tends to move or compress when being cut, rather than cut cleanly. Cutting tissue rather than removing it with a laser or other high energy device has the advantage of not overheating the tissue. This allows the tissue to be collected and its pathology tested, as previously described.

In some embodiments of the invention, the selective tissue cutting tool may be moved laterally along a tissue plane, removing thin swaths of tissue with each pass until the desired amount or type of tissue is removed. In some embodiments, the tool may be plunged into the target tissue in a distal direction, until a desired depth or type of tissue is reached. In any of these embodiments, the tool may cut a swath or bore that is as large as or larger than the width of the tool head. In some embodiments, the cutting elements are distally facing, laterally facing, or both.

According to further aspects of the present disclosure, in some embodiments the elongate member or shaft located between the distal housing and the motor assembly may be bendable. The elongate member may be incrementally or variably bendable. The bending may occur about a single point to form a constant radius bend. The bending may occur about multiple points in a single plane, such as when forming a variable radius bend or an S-curve. The bending may occur around multiple points in multiple planes, such as when forming compound bends. When the elongate member or shaft is capable of such bending, a tissue cutter assembly can approach and be oriented relative to target tissue sites not accessible by conventional debriders. These unique positioning modes enable medical procedures that otherwise could not be performed, or permit the procedures to be performed more easily. End effectors other than tissue cutter assemblies may be provided at the distal end of the bendable elongate member in a similar manner. For example, the end effector may be a tissue grasper having jaws that are driven between open and closed positions by rotating an inner drive tube.

Figure 8D:
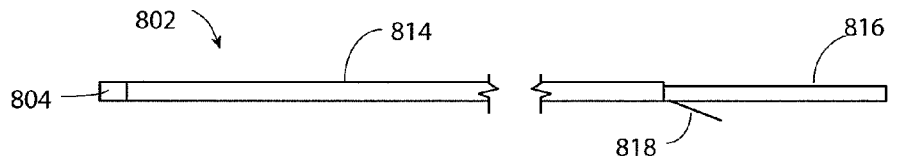
FIGS. 8A-8H schematically show the bendable aspects of another exemplary medical device.
Figure 8E:
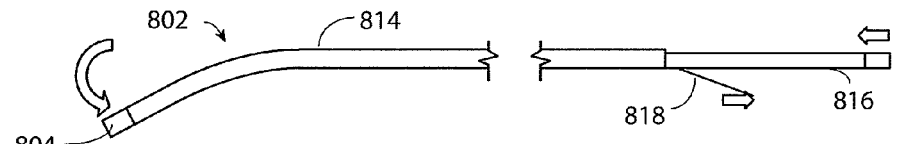
Figure 8F:
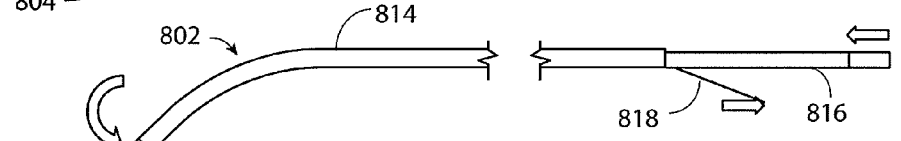
Figure 8G:
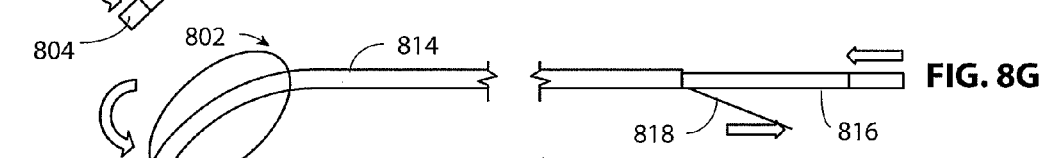
Figure 8A:
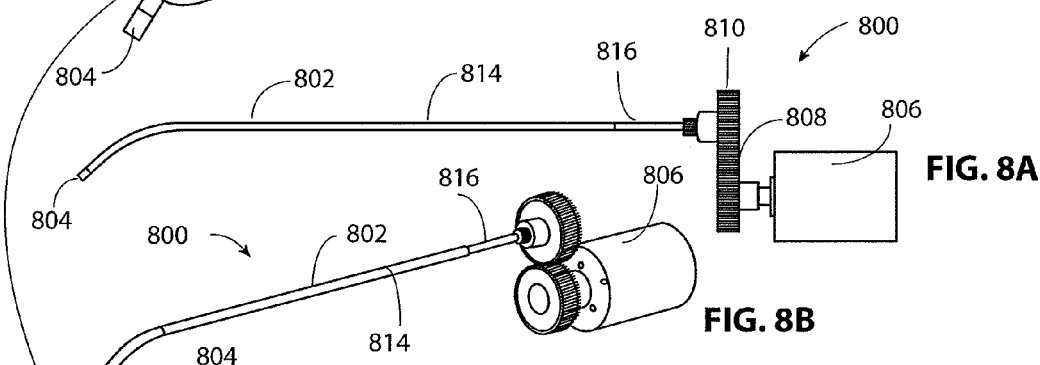
Figure 8B:
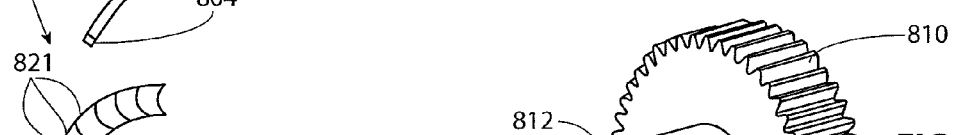
Figure 8C:
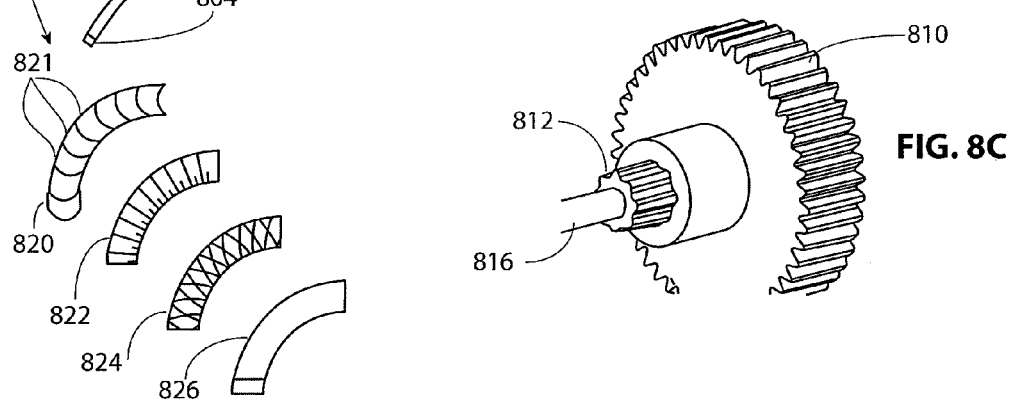

Referring to FIGS. 8A-8H, a bendable device 800 enabled by the present disclosure is schematically shown. As shown in FIGS. 8A and 8B, device 800 includes a bendable elongate member 802 having an end effector 804, such as a tissue cutter assembly, located at its distal end. As shown, elongate member 802 includes an outer support tube 814 and an inner drive tube 816. End effector 804 is rotatably driven by motor 806 through gears 808, 810 and inner drive tube 816. As best seen in FIG. 8C, the proximal end of inner drive tube 816 is provided with a spline 812. The center of gear 810 is provided with a complementary-shaped aperture for slidably receiving spline 812. This arrangement allows the proximal end of the inner drive tube 816 to move axially relative to gear 810 while still allowing gear 810 to rotatably drive inner drive tube 816.

Referring to FIGS. 8D-8G, elongate member 802 is schematically depicted in a series of configurations having various degrees of bending. As again shown, elongate member 802 includes an outer support tube 814 and an inner drive tube 816, both of which are bendable at least at their distal ends. In this exemplary embodiment, a pull cable 818 may be located along one side of the elongate member 802 between outer support tube 814 and inner drive tube 816 to effectuate the bending of elongate member 802. As pull cable 818 is drawn proximally, the distal end of the elongate member 802 moves from a straight configuration as shown in FIG. 8D to a bent configuration as shown in FIG. 8E. As pull cable 818 is drawn further proximally, elongate member 802 assumes the shapes shown in FIGS. 8F and 8G. A handle or knob with or without a locking member (not shown) may be coupled to the proximal end of the pull cable 818 to enable a user to pull the cable easily and lock the elongate member 802 in a bent position. While a single pull cable 818 is shown in FIGS. 8D-8G, in other embodiments multiple pull cables or other actuating mechanisms may be used to bend elongate member 802.

As depicted in FIGS. 8D-8G, as the distal end of the elongate member 802 is progressively bent, the proximal end of inner drive tube 816 is progressively drawn distally. This occurs in part because the distal end of inner drive tube 816 is constrained to move with end effector 804, as will be subsequently described in more detail. This also occurs because the bending of inner drive tube 816 may not happen along its neutral axis, but may be offset by the inward curve of outer support tube 814. The previously described axial movement of spline 812 relative to gear 810 allows the proximal end of inner drive tube 816 to move distally as elongated member 802 bends. As will be clear to those having ordinary skill in the art, other mechanisms for allowing the proximal end of inner drive tube 816 to float may be employed.

Figure 8H:
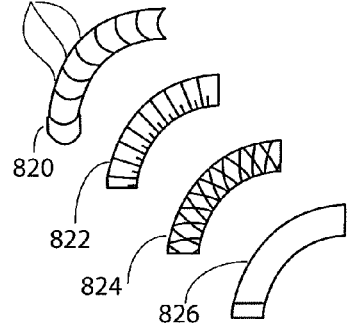

Referring now to FIG. 8H, various exemplary alternatives for allowing elongate member 802 to bend are shown. Elongate member 802 may be formed from or comprise one or more bendable segments 820. Bendable segment(s) 820 may comprise a series of interconnected links 821 that flex or pivot with respect to one another in one or more dimensions. Bendable segment(s) 822 may be provided with a series of cuts through the tube wall to allow the segment to bend. These cuts may be formed by sawing, milling, laser cutting, electric discharge machining (EDM), molding, or other fabrication techniques. Bendable segment(s) 824 may be formed by a wire braiding coated with or molded into an elastomeric sheath. Bendable segment(s) 826 may be formed from a shape memory alloy. The shape memory alloy may be formed in a preset shape, such as straight or curved, and then reshaped into a second configuration. By changing the temperature of the shape memory alloy, such as by applying an electrical current, the shape memory alloy may then be caused to return to the preset shape. These various bendable segment embodiments may be employed individually or in combination. For example, one section of elongate member 802 may comprise bendable segment 820 while another section of elongate member 802 may comprise bendable segment 822. By way of another example, outer support tube 814 may comprise bendable segment 820 while inner drive tube 816 may comprise bendable segment 824. Additionally, one or both of outer support tube 814 and inner drive tube 816 may be configured to be malleable so that elongate member 802 may be shaped by the surgeon before or during a procedure.

Figure 9A:
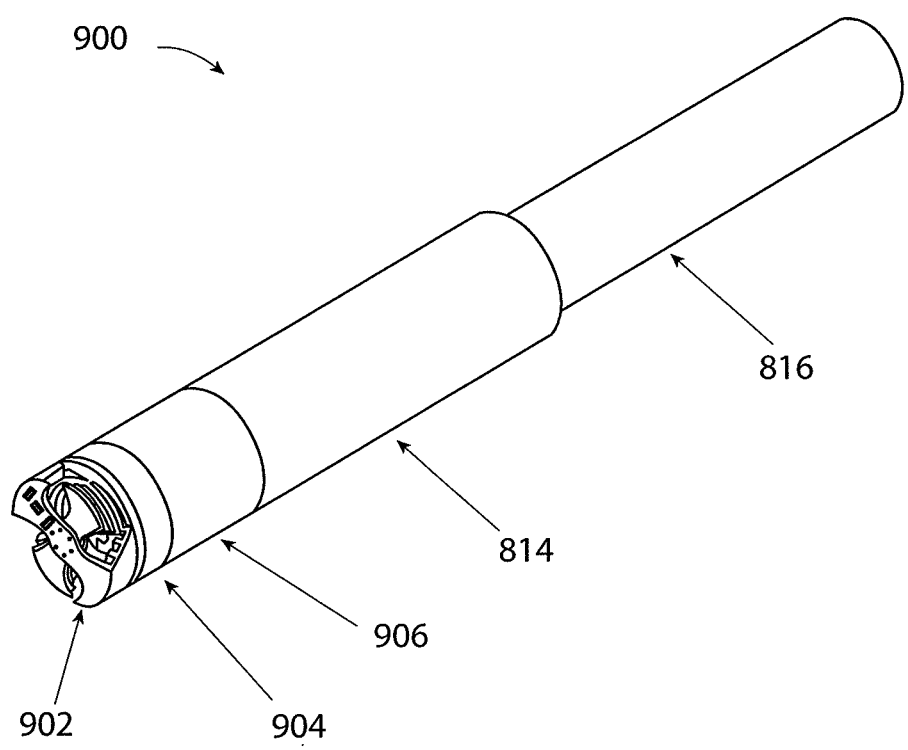
FIGS. 9A-9D are various views showing the distal end of a concentric end cutter device 900.
Figure 9B:
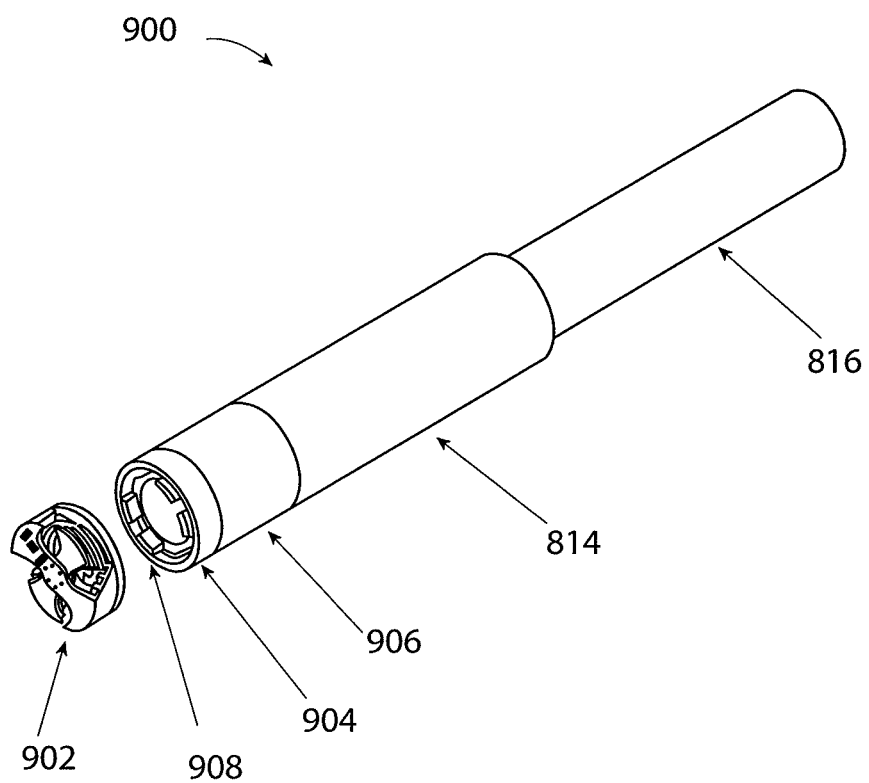
Figure 9C:
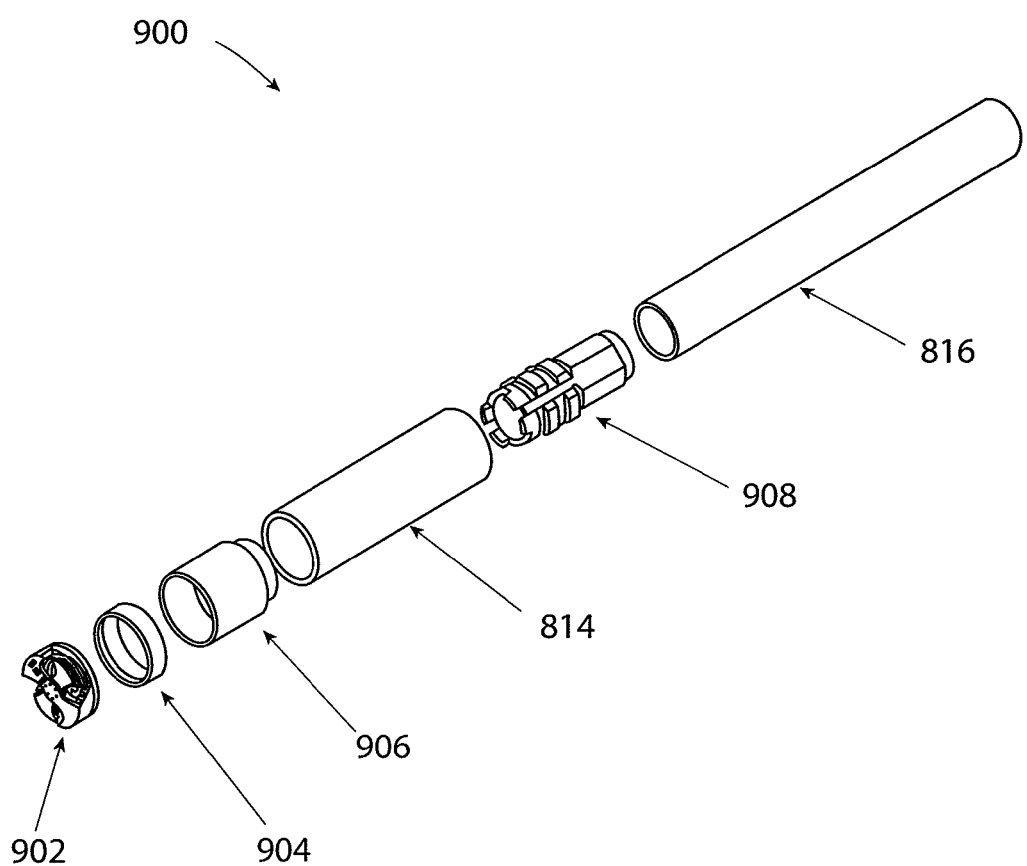
Figure 9D:
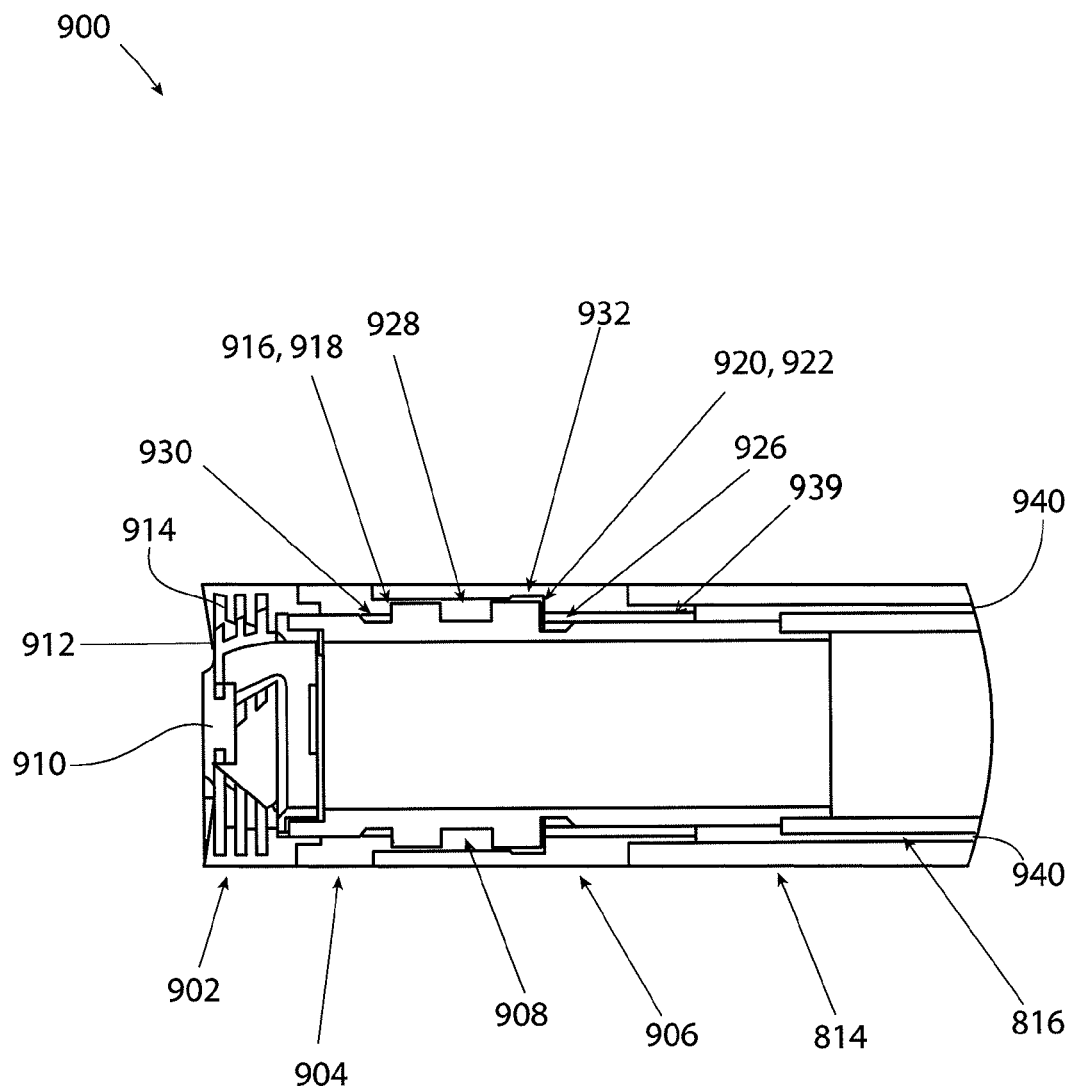

Referring to FIGS. 9A-9D, the distal end of a particular exemplary embodiment of a concentric end cutter device 900 is shown. FIG. 9A is a perspective view showing the distal end of device 900 in an assembled state. FIG. 9B is a perspective view showing the distal end of device 900 with cutter assembly 902 separated from the distal end of the elongate member. FIG. 9C is an exploded perspective view showing the individual components of device 900 disassembled. FIG. 9D is an enlarged side elevation view showing a cross-section of the distal end of device 900 taken along its longitudinal centerline. Device 900 includes a tissue cutter assembly 902, a thrust ring 904, a distal housing 906, an outer support tube 814, and an inner drive tube 816. Additionally, device 900 includes a coupler 908, as shown in FIGS. 9B-9D.

As shown in FIG. 9D, tissue cutter assembly 902 located at the distal end of device 900 includes a stationary housing 910, and a rotating blade assembly 912 rotatably and concentrically mounted therein. Stationary housing 910 includes inwardly protruding fins 914 that interdigitate with the disc shaped blades of rotating blade assembly 912 to create shearing surfaces for cutting tissue. The proximal end of stationary housing 910 mates with the distal end of thrust ring 904. The proximal end of thrust ring 904 mates with the distal end of coupler 908. The proximal end of coupler 908 mates with the distal end of outer tube 814. At each of these mating connections, the proximal end of the distal component may include a proximally extending shoulder sized to be received within a counterbore located on the distal end of the mating proximal component, as shown. Each shoulder may be press fit into the associated counterbore, and/or affixed thereto such as by adhesive or welding. Once assembled, as shown in FIGS. 9A and 9D, stationary housing 910, thrust ring 904, housing 906, and outer tube 814 form a single tubular structure wherein the individual components do not move with respect to one another. In a similar fashion, the proximal end of coupler 908 is affixed to the distal end of inner drive tube 816, as shown in FIG. 9D. As can be seen in FIGS. 9B and 9C, the distal end of coupler 908 maybe castellated. The proximal end of blade assembly 912 may include proximally extending tabs (not shown) that inter-engage with the castellations on the distal end of coupler 908. With this arrangement, rotating blade assembly 912 may be rotationally driven by coupler 908 but allowed to axially float with respect thereto. Thus, blade assembly 912, coupler 908, and inner drive tube 816 rotate concentrically within the previously described stationary components. Some or all of the stationary components 814, 906, 904 and 910 may collectively be referred to as a stator assembly. Some or all of the rotating components 816, 908 and 912 may collectively be referred to as a rotor assembly.

In this exemplary embodiment, coupler 908 serves many functions. Coupler 908 serves to rotationally couple the distal end of inner drive tube 816 to the proximal end of rotating blade assembly 912. Because of the fine tolerances between blade assembly 912 and stationary housing 910 of cutter 902, coupler 908 serves this function while being axially decoupled from blade assembly 912, as previously described. Coupler 908 also serves to constrain the axial movement of the distal end of inner drive tube 816 to allow inner drive tube 816 to remain rotationally coupled to blade assembly 912 when elongate member 802 is being bent, as previously described. Coupler 908 also serves to allow the distal flow of lubricating, cooling and irrigation fluid to tissue cutting assembly 902, and the return flow therethrough of irrigation fluid and cut tissue particles. Coupler 908 is also configured to permit adequate lubrication and cooling of mating axial surfaces and mating radial surfaces between coupler 908, housing 906 and thrust ring 904 during high rotational velocities. These features will be subsequently described in more detail.

As best seen in FIG. 9D, coupler 908 includes at least one forward thrust surface 916 that engages with at least one forward thrust surface 918 of thrust ring 904. Coupler 908 also includes at least one rear thrust surface 920 that engages with at least one rear thrust surface 922 of housing 906. Forward thrust surfaces 916 and 918 constrain coupler 908 and inner drive tube 816 from moving axially in a distal direction relative to outer support tube 814. Similarly, rear thrust surfaces 920 and 922 constrain coupler 908 and inner drive tube 816 from moving axially in a proximal direction relative to outer support tube 814. In some embodiments, the tolerances of device 900 may be selected such that an axial movement of less than 0.005 inches is permitted between coupler 908 and housing 906. In other embodiments, the tolerances of device 900 may be selected such that an axial movement of less than 0.001 inches is permitted. As shown in FIG. 10, the forward and rear thrust surfaces of coupler 908 may each be split into four segments by four axially extending irrigation ports 924. Rear thrust surface 922 of housing 906 is also shown in FIGS. 11A and 11B.

Referring to FIG. 10, coupler 908 may be provided with one or more circumferentially extending grooves to form fluid plenums. In this embodiment, a rearward groove 926 forms a first fluid plenum adjacent to rear thrust surfaces 920 and 922 when coupler 908 is assembled within housing 906, as shown in FIG. 9D. Similarly, a middle groove 928 forms a third fluid plenum, and a foreword groove 930 forms a fourth fluid plenum adjacent to forward thrust surfaces 916 and 918. Four axially extending irrigation ports 931 (two of which are shown in FIG. 10) may be provided between rearward groove 926 and the proximal end of coupler 908. Irrigation ports 931 may be circumferentially aligned with irrigation ports 924 as shown.

Referring to FIGS. 11A and 11B, a groove 932 may be provided radially within the inside wall of housing 906. Groove 932 forms a second fluid plenum adjacent rear thrust surfaces 920 and 922 when coupler 908 is assembled within housing 906, as shown in FIG. 9D. One or more axially extending channels may be provided across at least a portion of the inside wall of housing 906 for transporting lubricating, cooling and/or irrigation fluid in a distal direction. In this exemplary embodiment, four such channels 934 (three of which are shown in FIG. 11 B) may be spaced around the inner diameter of housing 906.

Referring to FIGS. 10, 11A and 11B, one or more solid regions 936 may be provided around the circumference of the proximal end of coupler 908, located between irrigation ports 931, as shown in FIG. 10. Similarly, one or more solid regions 938 may be provided around the inner diameter of the proximal end of housing 906, located between irrigation ports 934, as shown in FIG. 11B. In this exemplary embodiment, the proximal ends of coupler 908 and housing 906 may collectively be referred to as a commutator portion 939 (shown in FIG. 9D.) In other embodiments (not shown), the commutator portion may be formed by other portions of the rotor assembly and stator assembly. The outwardly facing solid regions 936 of coupler 908 are configured to bear against the inwardly facing solid regions 938 of housing 906. This bearing arrangement serves to radially constrain the proximal end of coupler 908 as it rotates within the proximal end of housing 906. Axially extending irrigation ports 931 on coupler 908 and axially extending irrigation ports 934 within housing 906 serve to transport lubrication, cooling and/or irrigation fluid in a distal direction across the commutator portion. More specifically, fluid is distally transported by ports 931 and 934 from an annular void 940 located between outer support tube 814 and inner drive tube 816, which is shown in FIG. 9D. Fluid is distally transported from annular void 942 to rearward groove 926 (the first fluid plenum) adjacent to rear thrust surfaces 920 and 922.

One or more solid regions 944 may be provided around the circumference of the distal end of coupler 908 located between circumferential grooves 926, 928 and 930, and between irrigation ports 924. In this exemplary embodiment, eight such solid regions 944 are provided, six of which are shown in FIG. 10. The outwardly facing solid regions 944 of coupler 908 are configured to bear against the inside diameter of the distal end of housing 906. This bearing arrangement serves to radially constrain the distal end of coupler 908 as it rotates within the distal end of housing 906. Beveled surfaces 946 may be provided on the leading and/or trailing edges of the outwardly facing solid regions 944 to force fluid from irrigation ports 924 between solid regions 944 and the inside diameter of the distal end of housing 906 for enhanced lubrication and cooling.

Figure 12A:
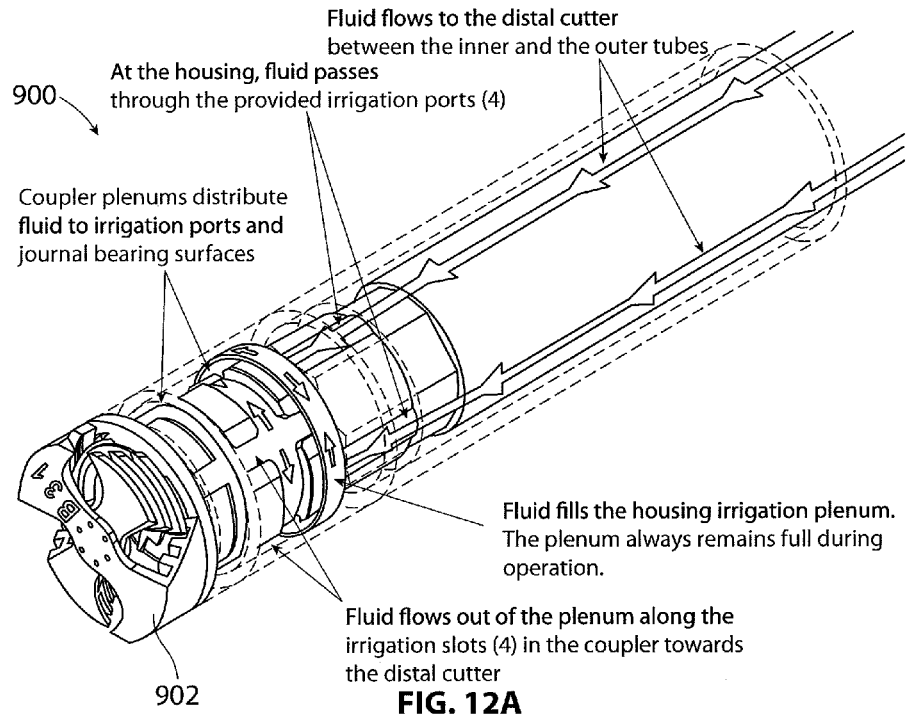
FIGS. 12A-12H are various views showing the flow of fluid through device 900.
Figure 12B:
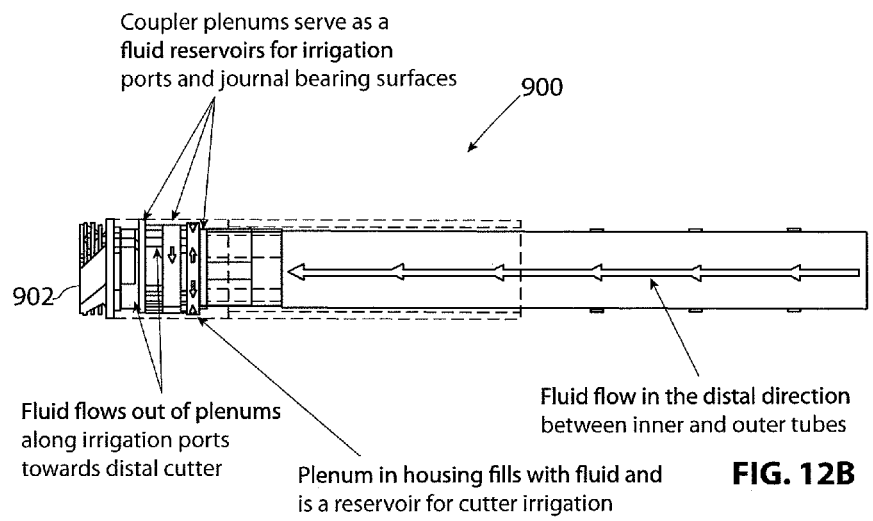
Figure 12C:
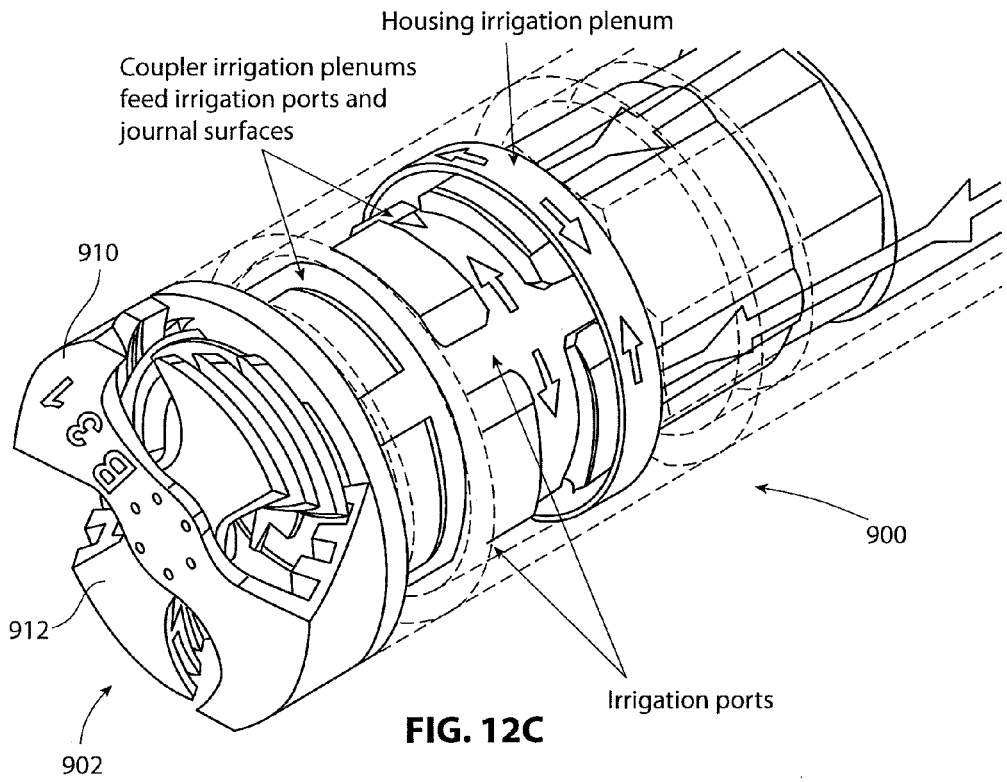
Figure 12D:
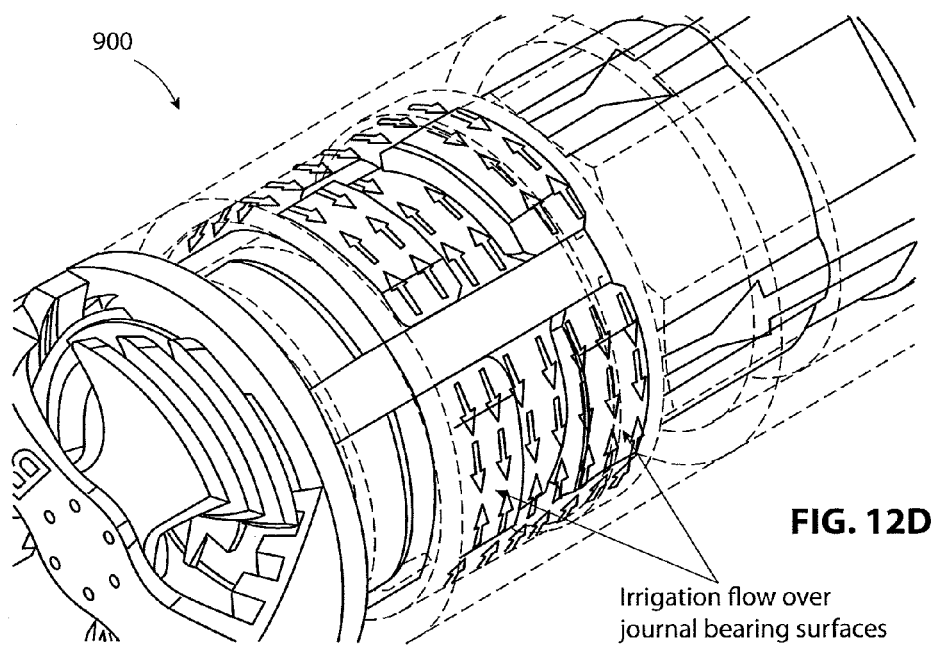
Figure 12E:
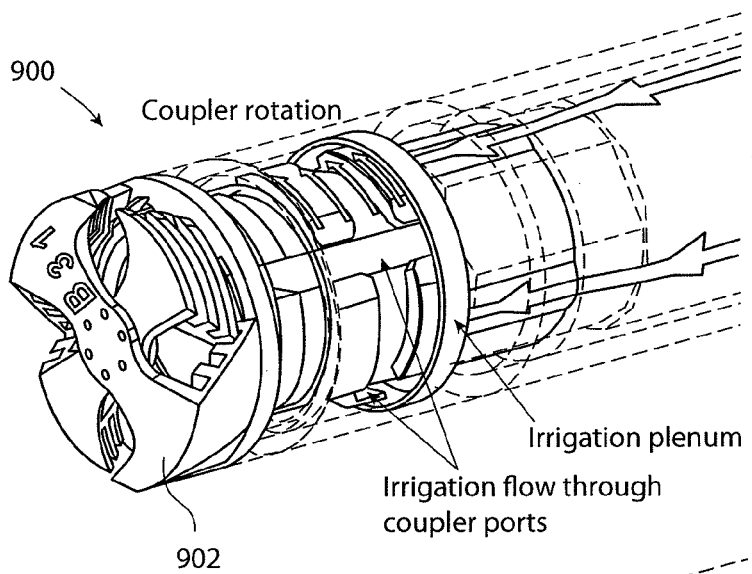
Figure 12F:
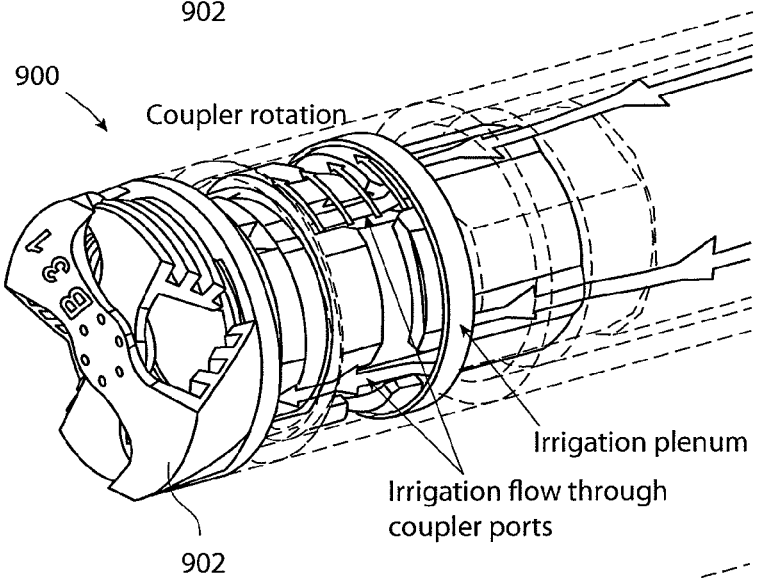
Figure 12G:
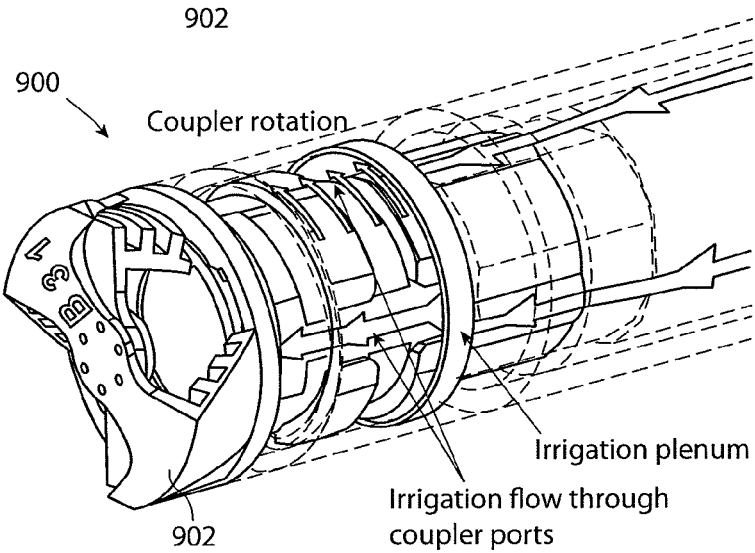
Figure 12H:
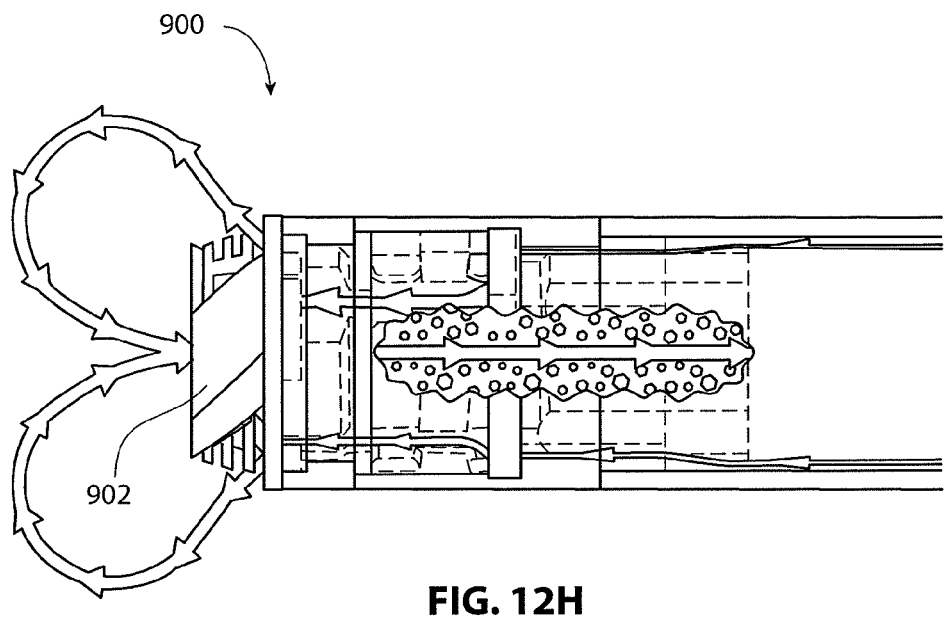

Referring to FIGS. 12A-12H, details regarding the flow of fluid during operation of exemplary device 900 will now be described. As previously indicated, fluid flows distally from the proximal end of the device through an annular void 940 located between inner drive tube 816 and outer support tube 814. When fluid reaches housing 906, it passes across a commutator portion by passing through axial irrigation ports 931 and 934. On the distal side of the commutator portion, the fluid fills channel 926 which forms the first fluid plenum adjacent to rear thrust surfaces 920 and 922. In some embodiments, the first plenum always remains full during operation. The plenums may serve to smooth out the otherwise pulsatile flow that may result from various axially extending fluid channels coming into and out of alignment with one another. The fluid flows further distally along irrigation ports 924 and is distributed to the journal bearings surfaces on the distal end of coupler 908 by irrigation ports 924 and middle groove 928. The fluid continues to flow distally into the fourth fluid plenum formed by distal groove 930 adjacent to the forward thrust surfaces 916 and 918. The fluid then flows distally out of the fourth fluid plenum along irrigation ports 924 and into cutter assembly 902. As shown in FIG. 12H, fluid flows radially out the sides of cutter assembly 902 and reenters a central region of cutter assembly 902, carrying with it particles of cut tissue as it flows proximally up the center of inner drive tube 816.

Figure 13A:
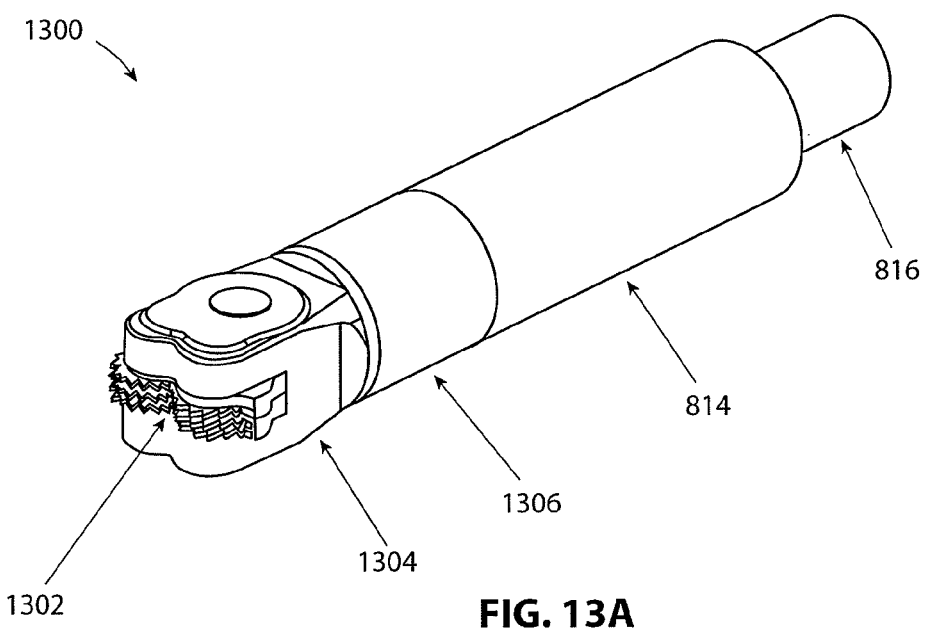
Figure 13B:
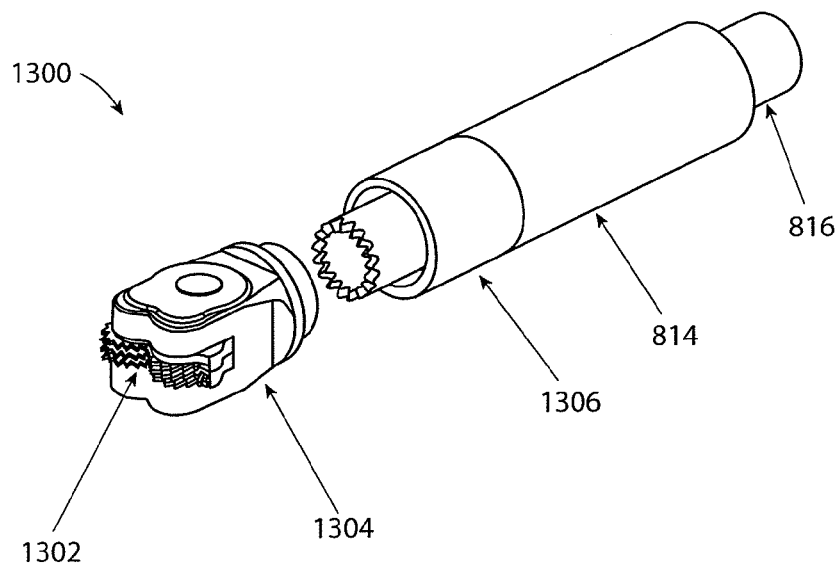
Figure 13C:
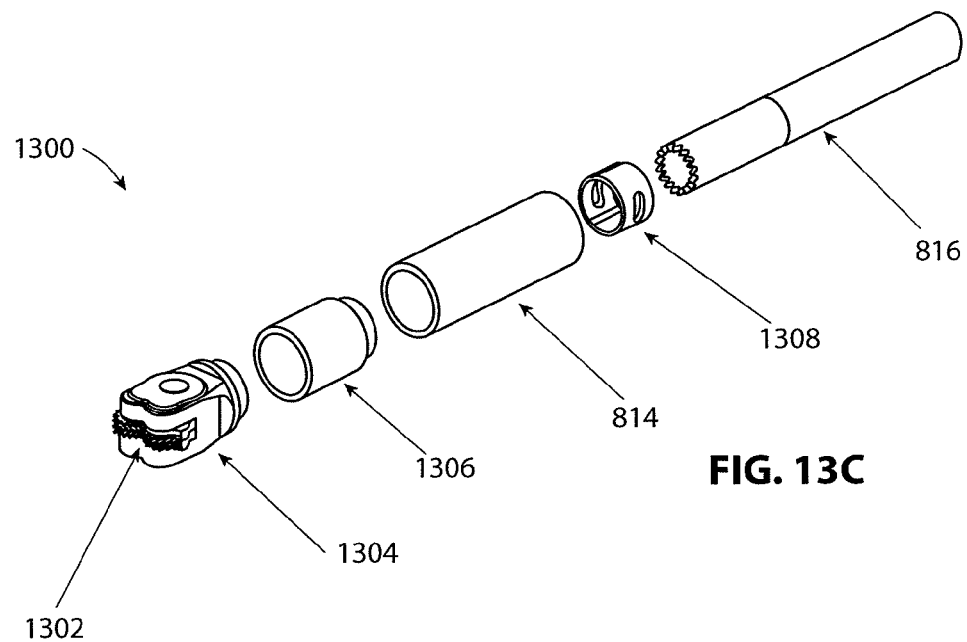

Referring to FIGS. 13A-13E, the distal end of a particular exemplary embodiment of a right angle tissue shredder 1300 is shown. FIG. 13A is a perspective view showing the distal end of device 1300 in an assembled state. FIG. 13B is a perspective view showing the distal end of device 1300 with cutter assembly 1302 separated from the distal end of the elongate member. FIG. 13C is an exploded perspective view showing the individual components of device 1300 disassembled. FIG. 13D is an enlarged top plan view showing a cross-section of the distal end of device 1300 taken along a longitudinal centerline. FIG. 13E is an enlarged side elevation view showing a cross-section of the distal end of device 1300 taken along a longitudinal centerline. Device 1300 includes a tissue cutter assembly 1302, a lug 1304, a housing 1306, an outer support tube 814, and an inner drive tube 816. Additionally, device 1300 includes a thrust ring 1308, as shown in FIGS. 13C-13E.

As shown in FIGS. 13D-13E, a tissue cutter assembly 1302 located at the distal end of device 1300 includes two oppositely rotating cutter blade assemblies 1310 rotatably mounted within lug 1304. The proximal end of lug 1304 mates with the distal end of housing 1306. The proximal end of housing 1306 mates with the distal end of outer tube 814. At each of these mating connections, the proximal end of the distal component may include a proximally extending shoulder sized to be received within the central bore of the mating proximal component, as shown. Each shoulder may be press fit into the associated bore and/or affixed thereto such as by adhesive or welding. Once assembled, as shown in FIGS. 13A, 13D and 13E, lug 1304, housing 1306 and outer tube 814 form a single tubular structure wherein the individual components do not move with respect to one another. As with previous embodiments, inner drive tube 816 is configured to rotate within outer tube 814. Inner drive tube 816 includes a crown gear located on its distal end for meshing with right angle gear 1312. Right angle gear 1312 in turn drives cutter blade assemblies 1310 through a gear drive train, as described in previous embodiments.

Referring to FIG. 14, an enlarged perspective view of thrust ring 1308 is provided. Thrust ring 1308 may include a rear thrust surface 1314 and/or a forward thrust surface 1316 as shown. Thrust ring 1308 may also be provided with one or more axially extending irrigation ports. In this exemplary embodiment, thrust ring 1308 includes two external irrigation ports 1318 and two internal irrigation ports 1320. Thrust ring 1308 is configured with a central bore for slidably receiving the outer diameter of inner drive tube 816. Thrust ring 1308 may be rigidly affixed to inner drive tube 816, such as by welding through the two circumferentially extending slots 1320 provided on opposite sides of thrust ring 1308 as shown.

Referring again to FIGS. 13D-13E, when thrust ring 1308 is rigidly affixed to inner drive tube 816, it's rear thrust surface 1314 contacts a rear thrust surface 1322 located on the inner diameter of housing 1306. The contact of rear thrust service 1314 of thrust ring 1308 against the rear thrust service 1322 of housing 1306 prevents the distal end of inner drive tube 816 from moving axially in a proximal direction beyond a predetermined rear location. In some embodiments, the distal end of inner drive tube 816 is prevented from moving axially in a distal direction beyond a predetermined forward location by the crown gear located at the distal end of inner drive tube 816 engaging with right angle gear 1312, which has its axial location fixed by way of being rotatably mounted to lug 1304. In other embodiments, the distal end of inner drive tube 816 is prevented from moving axially in a distal direction beyond a predetermined forward location by forward thrust surface 1316 of thrust ring 1308 contacting a forward thrust surface (not shown) on housing 1306 or lug 1304.

Referring to FIGS. 15A and 15B, enlarged perspective views of housing 1306 are shown. A circumferential groove 1324 may be provided around the inside diameter of housing 1306 to form a fluid plenum adjacent to rear thrust surface 1322. Axially extending fluid irrigation ports may also be provided along the inside diameter of housing 1306, such as four irrigation ports 1326 (three of which are shown in FIG. 15B.) Irrigation ports 1326 serve to transmit fluid distally from annular void 940 towards thrust ring 1308, as depicted in FIGS. 13D and 13E.

Figure 16B:
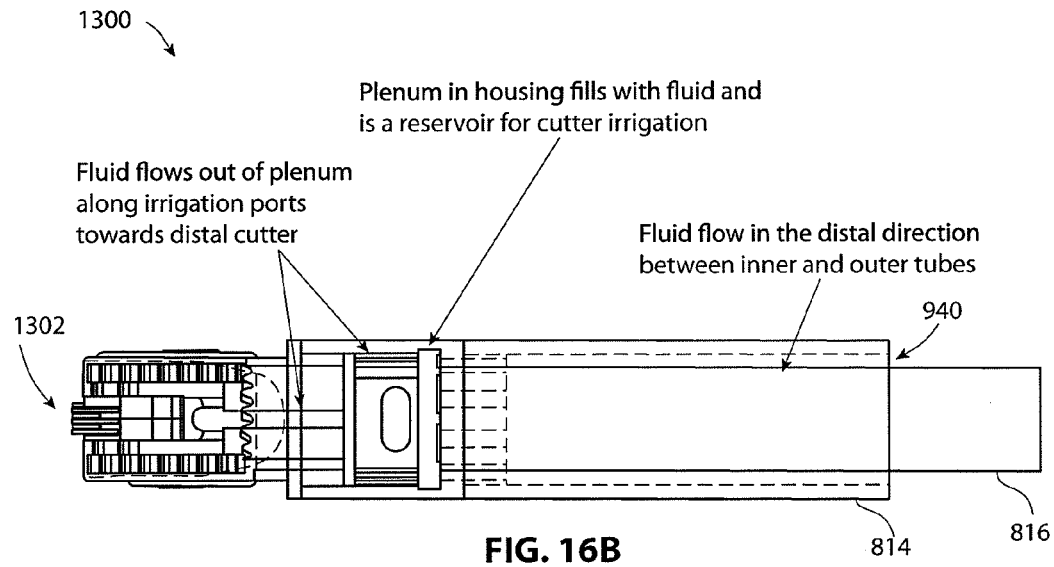
Figure 16C:
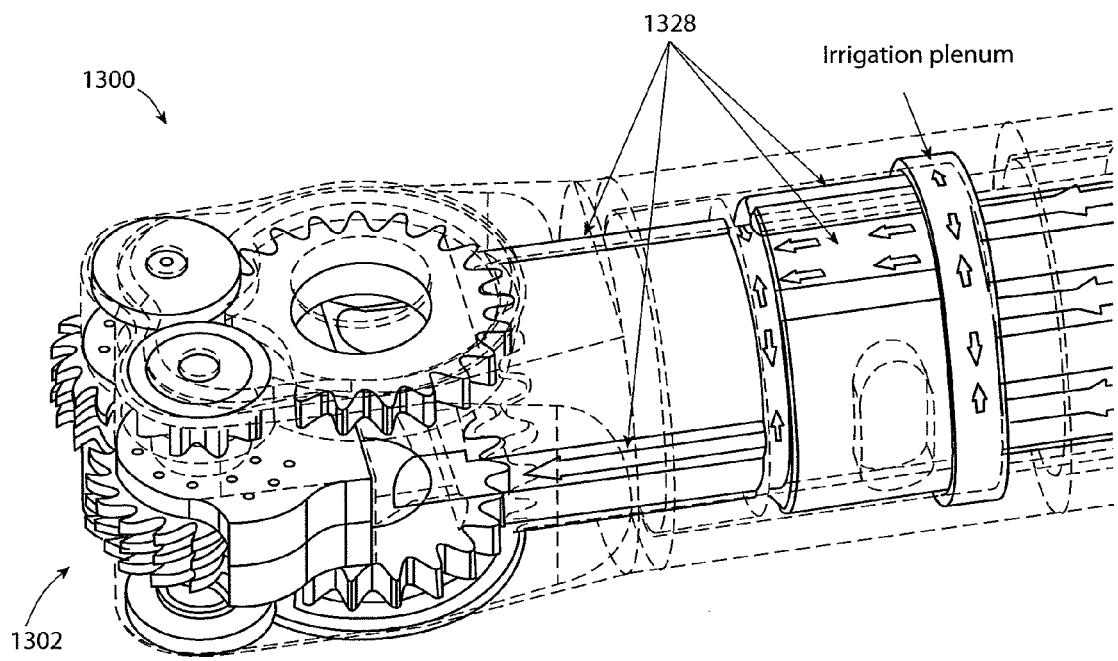
Figure 16D:
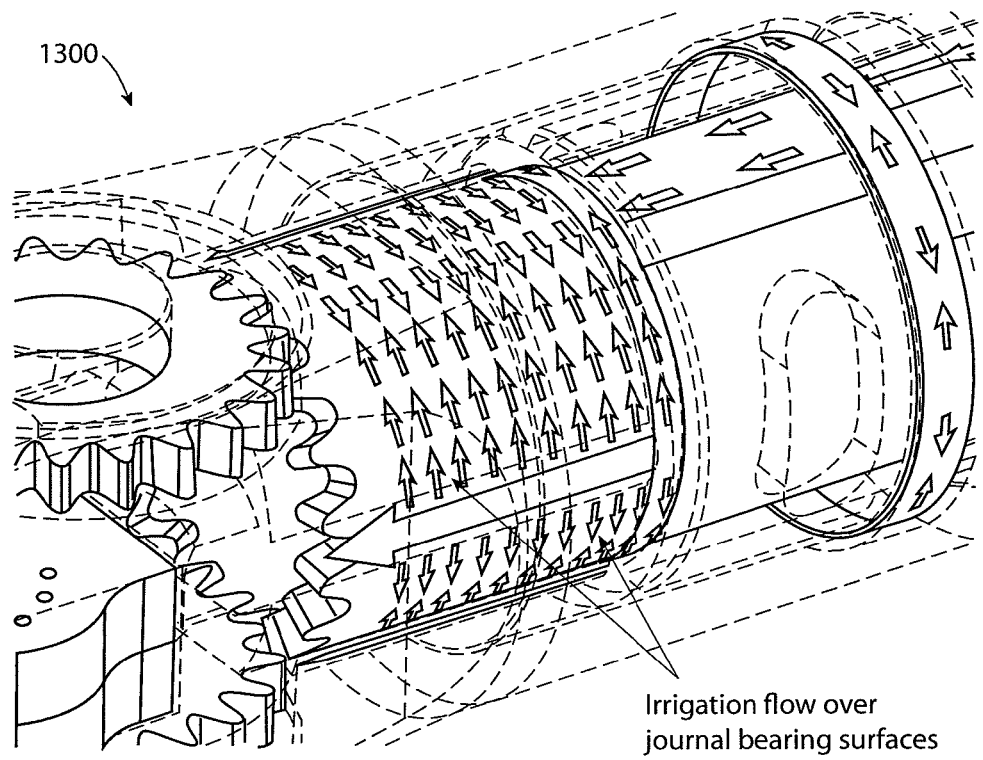
Figure 16E:
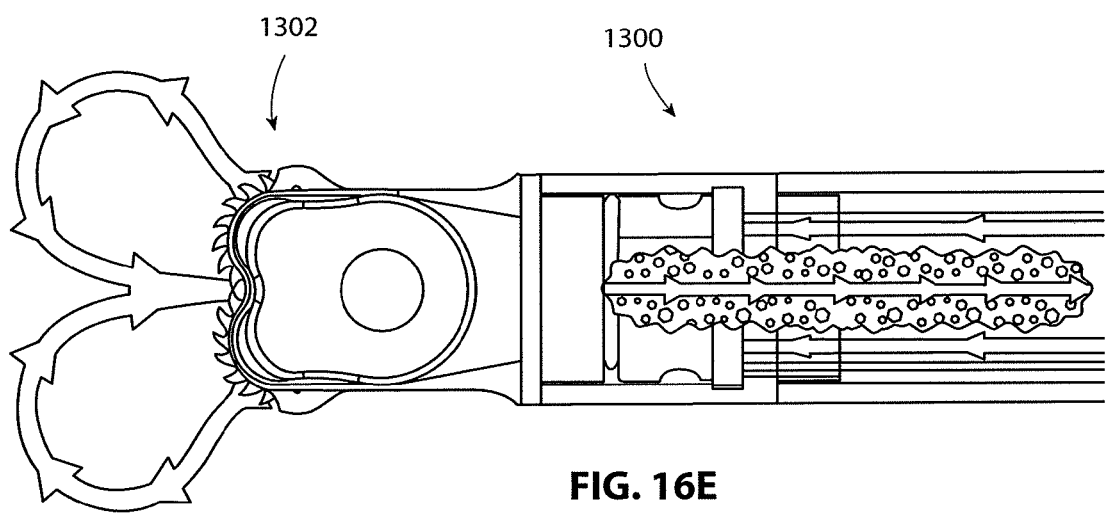

Referring to FIGS. 16A-16E, details regarding the flow of fluid during operation of exemplary device 1300 will now be described. As previously indicated, fluid flows distally from the proximal end of the device through an annular void 940 located between inner drive tube 816 and outer support tube 814. When fluid reaches housing 1306, it passes across a commutator portion by passing through axial irrigation ports 1326. On the distal side of the commutator portion, the fluid fills channel 1324 which forms a fluid plenum adjacent to rear thrust surfaces 1314 and 1322. In some embodiments, the plenum always remains full during operation. The plenum may serve to smooth out the otherwise pulsatile flow that may result from various axially extending fluid channels coming into and out of alignment with one another. The fluid flows out of the plenum and further distally along irrigation channels 1318 and 1320 that extend axially across thrust ring 1308. Fluid continues to travel distally towards cutter assembly 1302 by flowing through irrigation channels 1328 that axially extend across the inner diameter of the bore located in the proximal end of lug 1304, as best seen in FIG. 16C. Fluid also flows circumferentially from the irrigation channels 1328 across journal bearing surfaces inside the bore of lug 1304, as shown in FIG. 16D. Fluid passes through the gear drive train of cutter assembly 1302 before exiting from the sides of cutter assembly 1302. Fluid reenters a central region of cutter assembly 1302, carrying with it particles of cut tissue as it flows proximally up the center of inner drive tube 816, as shown in FIG. 16E.

The features of the embodiments described herein permit elongate medical devices to be bendable, as previously described in reference to FIGS. 8A-8H. As previously described, the distal end of the inner drive tube may be axially constrained, while the proximal end is allowed to float such that it can move axially relative to the proximal end of the outer tube. These features also allow elongate medical devices to be telescoping, such that the length of the device may be extended or shortened during a medical procedure. In some telescoping embodiments, the device may be configured to be bendable. In other telescoping embodiments, the device may be configured to be rigid, in either a straight or curved configuration. Additionally, these features also allow elongate medical devices to be hinged at one or more articulation points.

The distal constraining mechanisms disclosed herein allow for non-coupled engagement between drive shaft features and micro-machine features to be highly accurate for small features down to 10μ. In some embodiments, the constraining mechanism tightly locates the distal drive features down to 10μ while allowing the drive shaft to rotate and bend.

In some embodiments, outer shaft 814 has a diameter of 10 mm. In other embodiments, outer shaft 814 has a diameter of 5 mm. In still other embodiments, outer shaft 814 has a diameter of 1.5 mm or less.

In some embodiments, the features described herein permit the inner drive shaft to rotate within the outer shaft at a rate of at least 10,000 RPM. In some embodiments, the rotation rate may be up to 100,000 RPM. In some embodiments, the fluid running through the device is supplied at a pressure of between about 50 and about 200 PSI. In some embodiments, the fluid pressure is about 100 PSI. In general, the higher the fluid pressure the faster the inner drive shaft may be rotated. In some embodiments, a peristaltic pump is used to deliver the fluid through the device.

In view of the teachings herein, many further embodiments, alternatives in design and uses of the embodiments of the instant invention will be apparent to those of skill in the art. As such, it is not intended that the invention be limited to the particular illustrative embodiments, alternatives, and uses described above but instead that it be defined by the claims presented hereafter.

What is claimed is:

1. A medical device for removing tissue from a subject, comprising:
   a distal housing configured with a tissue cutter assembly;
   an elongate member coupled to the distal housing and configured to introduce the distal housing to a target tissue site of the subject, the elongate member having an outer tube, an inner drive tube rotatably mounted within the outer tube, and an annular void formed between the inner drive tube and the outer tube, wherein the outer tube and the distal housing form a stator assembly;
   a coupler located at a distal end of the inner drive tube and rotationally coupled therewith to form a rotor assembly, the coupler configured to engage with the tissue cutter assembly to rotatably drive the tissue cutter assembly, the coupler having a rear thrust surface configured to cooperate with a first surface on the stator assembly to prevent the inner drive tube from moving proximally beyond a predetermined rear location, the coupler having a forward thrust surface configured to cooperate with a second surface on the stator assembly to prevent the inner drive tube from moving distally beyond a predetermined forward location; and
   a commutator portion located between the rotor assembly and the stator assembly, the commutator portion having at least one solid region configured to rotatably support the rotor assembly relative to the stator assembly, the commutator portion having at least one fluid channel configured to allow passage of a fluid from the annular void, distally across the commutator portion, and into a first fluid plenum adjacent to the rear thrust surface and the first surface of the stator assembly;
   wherein the coupler and the distal housing form at least one passage therebetween that fluidically connects the first fluid plenum with a second fluid plenum adjacent to the forward thrust surface and the second surface of the stator assembly,
   wherein the device is configured to allow a fluid to flow distally through the annular void, through the at least one fluid channel in the commutator portion, through the first fluid plenum, through the at least one passage between the coupler and the distal housing, through the second fluid plenum, into at least a portion of the tissue cutter assembly, and proximally through the inner drive tube,
   wherein the device is configured to allow the fluid to lubricate and cool the forward and rear thrust surfaces and the tissue cutter assembly, and to transport tissue pieces cut by the tissue cutter assembly proximally through the inner drive tube,
   wherein the rotor assembly includes a third plenum axially located between the first plenum and the second plenum,
   wherein the third plenum is formed in the coupler and encircles the coupler.

* * * * *